United States Patent
Lister-James et al.

(10) Patent No.: US 6,358,491 B1
(45) Date of Patent: Mar. 19, 2002

(54) SOMATOSTATIN ANALOGS

(75) Inventors: John Lister-James; Richard T. Dean; Daniel A. Pearson, all of Bedford; David M. Wilson, Bow, all of NH (US)

(73) Assignee: Berlex Laboratories, Inc., Montville, NJ (US)

( * ) Notice: Subject to any disclaimer, the term of this patent is extended or adjusted under 35 U.S.C. 154(b) by 0 days.

(21) Appl. No.: 09/397,792

(22) Filed: Sep. 16, 1999

Related U.S. Application Data

(60) Provisional application No. 60/151,001, filed on Aug. 27, 1999.

(51) Int. Cl.$^7$ .......................... A61K 51/00; A61M 36/14
(52) U.S. Cl. .................... 424/1.69; 424/1.11; 424/1.65; 424/9.1; 530/311; 530/317; 530/329; 534/10; 534/14
(58) Field of Search ................................ 424/1.11, 1.65, 424/1.69, 9.1, 9.3, 9.4, 9.5, 9.6, 9.7, 9.8; 530/300, 311, 317, 324–330; 534/7, 10–16; 206/223, 569, 570

(56) References Cited

U.S. PATENT DOCUMENTS

| | | |
|---|---|---|
| 4,310,518 A | 1/1982 | Freidinger |
| 4,486,415 A | 12/1984 | Freidinger |
| 5,597,894 A | 1/1997 | Coy et al. |
| 5,708,135 A | 1/1998 | Coy et al. |
| 5,770,687 A | 6/1998 | Hornik et al. |
| 5,776,894 A | 7/1998 | Albert et al. |
| 5,830,431 A | 11/1998 | Srinivasan et al. |

FOREIGN PATENT DOCUMENTS

| | | |
|---|---|---|
| EP | 0 143 307 A2 | 6/1985 |
| EP | 0 222 578 | 5/1987 |
| EP | 0 714 911 A2 | 6/1996 |
| WO | WO 96/37239 | 11/1996 |
| WO | WO 97/01579 | 1/1997 |
| WO | WO 98/41540 | 9/1998 |

OTHER PUBLICATIONS

Anderson, et al. (1996) "Radiotherapy Studies of Cu–64–Labeled Teta–Octreotide in Tumor–Bearing Rats" Jnl. Nucl. Med., 128P.

Bass, et al. (1998) "Identification of the Soluble in Vivo Metabolites of Indium–111–Diethylenetriaminepentaacetic Acid–D–Phe1–Octreotide" Bioconjugate Chem., 9: 192–200.

Bernard, et al. (1997) "D–Lysine Reduction of Indium–111 Octreotide and Yttrium–90 Octreotide Renal Uptake" Jnl. Nucl. Med., 38: 1929–1933.

Blum, et al. (1999) "The Utility of a Somatostatin–Type Receptor Binding Peptide Readiopharmaceutical (P829) in the Evaluation of Solitary Pulmonary Nodules" Chest, 115: 224–232.

Bogden, et al. (1997) "Proliferative response of human and animal tumours to surgical wounding of normal tissues; onset duration and inhibition" British Jnl. of Cancer, 75(7) 1021–1027.

Breemen, et al. (1998) "Somatostatin receptor scintigraphy using [ 111–In–DTPA]Rc–160 in humans: a comparison with [111In–DTPA]octreotide" Eur.J.Nucl.Med. 25: 182–186.

De Jong, et al. (1998) "Pre–Clinical Comparison of [DTPA0]Octreotide, [DTPA0,Tyr3] Octreotide and [DOTA0,Tyr3] Octreotide as Carriers for Somatostatin Receptor–Targeted Scintigraphy and Radionuclide Therapy" Int. Jnl. Cancer, 75: 406–411.

Hammond, et al. (1993) "Amino acid infusion blocks renal tubular uptake of an indium–labelled somatostatin analogue" British Jnl. of Cancer, 67: 1437–1439.

Handmaker, et al. (1998) "Comparison of a Technetium Labeled SSTR Binding Peptide (P829) and F–18 FDG PET in the Evaluation of Solitary Pulmonary Nodules" Oncology Diagnosis: Non–Antibody Posters, 39(10): 315P.

Handmaker, et al. (1998) "Comparison of a Technetium Labeled SSTR Binding Peptide (P829) and Miraluma in the Diagnosis of Breast Cancer" Oncology Diagnosis: Non–Antibody Posters, 39(10): 315P.

Krenning, et al. (1994) "Radiotherapy with a Radiolabeled Somatostatin Analogue", [111In–DTPA–D–Phe1]–Octreotide Annals New York Academy of Sciences, 73: 496–506.

Lamberts, et al. (1996) "Octreotide" New England Jnl. of Med., 334(4): 246–254.

Leimer, et al. (1998) "Response to Treatment with Yttrium 90–DOTA–Lanreotide of a Patient with Metastatic Gastrinoma" Jnl. of Nucl. Med., 39(12): 2090–2094.

Otte, et al. (1997) DOTATOC: a powerful new tool for receptor–mediated radionuclide therapy European Jnl. of Nucl. Med., 24(7): 792–795.

(List continued on next page.)

Primary Examiner—Dameron L. Jones
(74) Attorney, Agent, or Firm—Tatsuya Ikeda; Patricia McDaniels; Millen, White, Zelano, and Branigan, P.C.

(57) ABSTRACT

The invention provides novel peptide-based pharmacophores and compounds which bind somatostatin receptors with high affinity and which exhibit improved pharmacokinetic properties over known somatostatin analogs. The pharmacophores and compounds of the invention may be used in labeled or unlabeled form for diagnosing and/or treating somatostatin responsive diseases. The invention also provides radiopharmaceuticals and kits comprising these compounds, as well as methods for diagnosing and/or treating somatostatin receptor mediated diseases.

45 Claims, No Drawings

OTHER PUBLICATIONS

Virgolini, et al., (1998) "Indium–111–DOTA–Lanreotide: Biodistribution, Safety and Radiation Absorbed Dose in Tumor Patients" Jnl. Nucl. Med., 39(11): 1928–1936.

Woltering, et al. (1997) "Somatostatin analogs: angiogenesis inhibitors with novel mechanisms of action" Investigational New Drugs, 15: 77–86.

Patel, et al. (1997) "Somatostatin Receptors" TEM, 8(10): 398–405.

Raynor, et al. (1993) "Cloned Somatostatin Receptors: Identification of Subtype–Selective Peptides and Demonstration of High Affinity Binding of Linear Peptides" Molecular Pharmacology, 43: 838–844.

Seregni, et al. (1998) "Radionuclide imaging of neuroendocrine tumours: biological basis and diagnostic results" European Jnl. Nucl. Med., 25: 639–658.

Stolz, et al. (1996) "Somatostatin Analogues for Somatostatin–Receptor–Mediated Radiotherapy of Cancer" Digestion, 57(suppl 1): 17–21.

Stolz, et al. (1998) "The somatostatin receptor–targeted radiotherapeutic [90Y–DOTA–DPhe1, Tyr3]octreotide (90Y–SMT 487) eradicates experimental rat pancreatic CA 20948 tumours" European Jnl. of Nucl. Med., 25(7): 668–674.

Virgolini, (1997) "Receptor nuclear medicine: vasointestinal peptide and somatostatin receptor scintigraphy for diagnosis and treatment of tumour patients" European Jnl. of Clinical Investigation, 27: 793–800.

SOMATOSTATIN ANALOGS

This application is a continuation-in part of provisional application serial No. 60/151,001, filed Aug. 27, 1999.

This application relates to the field of cancer imaging and therapy using novel somatostatin analogs.

BACKGROUND OF THE INVENTION

Cancer is a leading cause of morbidity and mortality in developed countries. For example, approximately 1.4 million new cases of cancer and more than 0.5 million cancer deaths were reported in the U.S. in 1996. In 1995, the total annual cost of cancer care in the U.S., including direct and indirect costs, was estimated to be more than $96 billion. A great need exists for improved diagnostic and therapeutic tools to allow early detection and safe, cost-effective treatment of cancer.

Many tumors express receptors for the peptide hormone somatostatin. In particular, neuroendocrine tumors such as pituitary adenomas, pheochromocytomas, paragangliomas, some medullary thyroid carcinomas, and some small cell lung cancers express somatostatin receptors (SSTRs). In addition, cells of nervous system tumors such as astrocytomas and meningiomas display SSTRs on their surfaces. SSTR expression has also been found in human breast tumors, malignant lymphomas, and renal cell carcinomas, and some prostate tumors may be characterized by SSTR expression.

Binding studies performed with radiolabeled or iodinated somatostatin and its analogs have identified five SSTR subtypes ($SSTRs_{1-5}$). The SSTR-bearing tumors described above express $SSTR_2$ and $SSTR_5$ most frequently, with $SSTR_3$ and $SSTR_4$ occurring less frequently, according to most authors. One group reports that $SSTR_3$ is expressed at very high levels in almost all human tumors (Virgolini (1997) *Eur. J. Clin. Invest.* 27, 793–800). There is general agreement that most tumors typically express more than one SSTR subtype, and that varying densities of SSTRs may be expressed in the cells contained within a particular tumor. The availability of cloned SSTR subtype genes has allowed somatostatin analogs to be characterized by their affinities for $SSTR_{1-5}$, and these studies have revealed considerable variability in SSTR subtype specificity among somatostatin analogs, as described in Raynor, et al. (1993) *Molecular Pharmacol.* 43, 838–844 and in Patel, et al. (1997) *TEM* 8, 398–404.

Until recently, three somatostatin analogs have been commercially available. Octreotide (Sandostatin®) binds to $SSTR_2$, $SSTR_3$, and $SSTR_5$, and is marketed in the U.S. and Europe for treatment of acromegaly and control of symptoms associated with vipomas and metastatic carcinoid tumors. Lanreotide (Somatuline™) has a SSTR subtype profile similar to that of octreotide and is approved in several European countries for the same indications as octreotide. A radiolabeled form of octreotide, $^{111}$In-pentetreotide ($^{111}$In-DTPA-D-Phe$^1$-octreotide or $^{111}$In-OctreoScan®) has been approved in the U.S. and Europe for imaging neuroendocrine tumors.

Recently the U.S. Food and Drug Administration approved a new radiopharmaceutical, NeoTect™, a $^{99m}$Tc-labeled form of the novel somatostatin analog depreotide (P829), for sale as an imaging agent. Blum, et al., (1999) *Chest* 115, 224–232, describes the use of $^{99m}$Tc-depreotide for evaluation of solitary pulmonary nodules of the lung. $^{99m}$Tc-labeled depreotide has also been studied as an imaging agent for other somatostatin-receptor bearing tumors.

For example, Handmaker (1998) *J. Nucl. Med.* 39, 315P describes a comparison of $^{99m}$Tc-depreotide and $^{99m}$Tc-sestamibi for diagnosis of breast cancer. Depreotide is described in commonly assigned U.S. Pat. No. 6,051,206, in U.S. Ser. No. 08/253,973; and in WO 95/00553 and WO 95/33497.

A large body of literature exists relating to clinical uses of unlabeled octreotide and lanreotide. For example, as summarized in Lamberts, et al. (1996) *New England J. of Med.* 334, 246–254, octreotide has been investigated for use in treating thyrotropin-secreting pituitary adenomas, nonsecretory pituitary adenomas, and corticotropin-secreting pituitary adenomas such as bronchial and thymic carcinoids, medullary thyroid carcinomas and pancreatic islet cell tumors, but not those not associated with Cushing's disease. Lamberts, et al. discloses that in general, octreotide treatment only occasionally resulted in transient inhibition of tumor growth. Lamberts, et al. further discloses that octreotide has also been studied for use in gastrointestinal and pancreatic diseases, with variable results: for example, octreotide was not effective in treating bleeding from peptic ulcers, but was effective in controlling bleeding from esophageal varices. Lamberts, et al. describes octreotide as being ineffective in the treatment of acute pancreatitis, but efficacious in reducing fluid production by pancreatic fistulas and pseudocysts. Clinical trials of octreotide for treatment of watery diarrhea in AIDS patients were also described in Lamberts, et al. Octreotide has also been studied as an anti-angiogenic agent, as summarized in Woltering, et al. (1997) *Investigational New Drugs* 15, 77–86. Lanreotide has been applied to surgical wounds induced in tumor-implanted mice to study its effect on wound-induced acceleration of tumor growth, and its use has been suggested as an endocrine antisecretogogue in cytoreductive cancer treatment, in Bogden, et al. (1997) *Brit. J. Cancer* 75, 1021–1027.

Despite the commercial availability of octreotide, lanreotide, and pentetreotide, a large number of somatostatin analogs have been proposed for use as imaging and/or therapeutic agents to detect and/or treat cancer and other somatostatin-responsive disease states. Patel, et al., supra, discloses the need for second generation somatostatin analogs which bind more selectively, i.e., with higher affinity, to SSTRs generally and to SSTR subtypes, in particular to $SSTR_1$, $SSTR_3$, and $SSTR_4$. Higher affinity analogs for $SSTR_2$ and $SSTR_5$ are also desirable, so that lower dosages of somatostatin analogs may be administered to obtain a clinical response.

Second generation somatostatin analogs are described, for example, in commonly assigned U.S. Pat. Nos. 5,620,675; 5,716,596; 5,783,170; 5,814,298; 5,820,845; 5,833,942; 5,843,401; 5,871,711; 5,932,189; allowed U.S. Ser. Nos. 08/592,323; 08/586,670; 08/776,160; 08/931,095; 09/039,062; 09/039,116; 09/042,224 and 09/042,315; and copending U.S. Ser. No. 08/092,355. U.S. Pat. No. 5,597,894 discloses somatostatin analogs containing additional N-terminal amino acids. U.S. Pat. Nos. 4,310,518 and 4,486,415 and EP 143 307 and EP 222 578 disclose cyclic hexapeptide somatostatin analogs which are cyclized through peptide linkages. U.S. Pat. No. 5,708,135 discloses somatostatin analogs which are cyclized through a disulfide bond between the N-terminal residue and the C-terminal residue. U.S. Pat. No. 5,776,894 discloses somatostatin peptides having a chelating group covalently linked to an N-terminal amino group. U.S. Pat. No. 5,770,687 discloses conformationally constrained backbone cyclized somatostatin analogs. U.S. Pat. No. 5,830,431 discloses radiolabeled somatostatin analogs having carboxyl termini in the carboxylic acid form. EP 714 911 discloses DOTA-conjugated octreotide analogs. WO 96/37239 discloses [188]Re-labeled vapreotide. WO 97/01579 discloses cyclic hexapeptide somatostatin analogs having a chelating group attached to a side chain amino group of a designated amino acid. Even in light of the large number of second generation somatostatin analogs which has been proposed, research continues for somatostatin analogs with improved binding properties.

Radiolabeled forms of octreotide and lanreotide have been investigated for use as radiotherapeutic agents in preclinical and clinical studies. For example, Anderson, et al. (1996) *J. Nucl. Med.* 37, 128P-129P, discloses a study of $^{64}$Cu-labeled TETA-octreotide as a radiotherapeutic in a tumor-bearing rat model. Stolz, et al. (1996) *Digestion* 57 (suppl. 1) 17–21, discloses $^{90}$Y-DTPA-benzyl-acetamido-D-Phe$^1$, Tyr$^3$-octreotide in a tumor-bearing mouse model. Otte, et al. (1997) *Eur. J. Nucl. Med.* 24, 792–795, discloses use of $^{90}$Y-labeled DOTA-D-Phe$^1$, Tyr$^3$-octreotide to treat metastatic neuroendocrine disease in one human patient. Krenning, et al. (1994) *Annals of N. Y. Acad. Sci.* 733, pp. 496–506, describes radiotherapy of a patient with a neuroendocrine tumor using therapeutic doses of $^{111}$In-DTPA-D-Phe-octreotide. DeJong, et al. (1998) *Int. J. Cancer* 75, 406–411, discloses a preclinical comparison of {DTPA}-octreotide, {DTPA, Tyr$^3$}-octreotide, and {DOTA, Tyr$^3$}-octreotide labeled with $^{111}$In and $^{90}$Y. Breeman, et al. (1998) *Eur. J. Nucl. Med.* 25, 182–186, describes a comparison of $^{111}$In-DTPA-RC-160 (vapreotide) and $^{111}$In-DTPA-octreotide for somatostatin receptor scintigraphy in humans. WO 98/41540 discloses DOTA-lanreotide for labeling with $^{111}$In, $^{90}$Y, $^{86}$Y, $^{67/68}$Ga, $^{161}$Tb, and $^{153}$Sm. Virgolini, et al. (1998) *J. Nucl. Med.* 39, 1928–1936, describes biodistribution of $^{111}$In-DOTA-lanreotide in humans. Leimer, et al. (1998) *J. Nucl. Med.* 39, 2090–2094, describes treatment of a metastatic carcinoma in a human patient using $^{90}$Y-DOTA-lanreotide. Preliminary data indicate that when labeled with a radionuclide having sufficiently energetic emissions, octreotide and lanreotide may be effective antitumor agents for somatostatin receptor-bearing tumors.

A frequently observed phenomenon with radiolabeled peptides is retention in a non-target organ such as kidney, liver, or spleen. When short-lived, relatively low energy isotopes such as $^{99m}$Tc are employed, kidney retention generally does not present a clinical problem. However, use of peptides labeled with isotopes having higher energies and/or longer half-lives, such as those proposed for use in radiotherapy, could result in an unacceptably high radiation dose to the non-target organ. Indeed, Breeman, et al., supra, concludes that the high kidney, liver, spleen, and lung background of $^{111}$In-DTPA-vapreotide rendered the compound unsuitable for scintigraphy. Retention of radiolabeled peptides in non-target organs limits the amount of radioactivity which can be administered.

Bernard, et al. (1997) *J. Nucl. Med.* 38, 1929–1933 discloses that significant amounts of $^{111}$In-DTPA-octreotide and $^{90}$Y-DOTA-octreotide accumulate in the renal parenchyma when administered to normal rats. Bass, et al. (1998) *Bioconjugate Chem.* 9, 192–200, discloses that $^{111}$In-DTPA-octreotide is retained in liver and kidney of normal and tumor-bearing rats. Virgolini, et al., supra, discloses that at 24 hours post-injection, $^{111}$In-DOTA-lanreotide is retained in human liver to about the same extent as $^{111}$In-DTPA-D-Phe$^1$-octreotide (about 3.2% injected dose); in spleen to a smaller extent (about 1.2% injected dose for $^{111}$In-DOTA-lanreotide compared to about 3% injected dose for $^{111}$In-DTPA-D-Phel-octreotide); and in kidney to a smaller extent (about 2.5% injected dose for $^{111}$In-DOTA-lanreotide compared to about 3.7% injected dose for $^{111}$In-DTPA-D-Phe$^1$-octreotide). Leimer, et al., supra, reports $^{90}$Y kidney doses of 1.98–2.43 mGy/MBq and spleen doses of 1.68–3.35 mGy/MBq in the patient treated with four cycles of $^{90}$Y-DOTA-lanreotide treatment.

Several approaches have been suggested to minimize the accumulation of radiolabeled peptides in non-target organs. Use of D- or L-lysine to reduce renal uptake of antibodies and/or peptides is disclosed in U.S. Pat. Nos. 5,380,513; 5,648,059; and 5,843,894. Stolz, et al. (1998) *Eur. J. Nucl. Med.* 25, 668–674, discusses use of kidney-specific cleavable linkers to enhance excretion of radiolabeled peptides but suggests using prior injection of L-lysine to lower the kidney radiation dose resulting from administration of $^{90}$Y-DOTA-D-Phe$^1$, Tyr$^3$-octreotide. Bernard, et al., supra, teaches that high doses of L-lysine may result in toxicity and suggests use of D-lysine to reduce accumulation of $^{111}$In-DTPA-octreotide and $^{90}$Y-DOTA-octreotide in kidneys. Hammond, et al. (1993) *Brit. Cancer J.* 67, 1437–1439, teaches infusion of a mixture of lysine and arginine to prevent kidney uptake of $^{111}$In-pentetreotide in human patients.

Although infusion of amino acids reduces kidney uptake of radiolabeled somatostatin analogs, the potential exists that the infused amino acids may themselves result in toxicity. In addition, currently there are no commercially available amino acid infusates with sufficiently high concentrations of lysine to effectively reduce kidney uptake of radiolabeled somatostatin analogs. A decrease in renal accumulation of a radiolabeled somatostatin analog would allow administration of a higher radiation dose, and thus more effective tumor ablation would be expected.

Thus a need remains for novel somatostatin analogs with improved affinity for SSTRs and improved pharmacokinetic properties.

SUMMARY OF THE INVENTION

The present inventors have designed novel SSTR pharmacophores which are structurally distinct from all previously known somatostatin analogs. The novel pharmacophores of the invention exhibit high affinity for SSTRs and consequently high tumor uptake. The inventors have also discovered novel metal ion chelators, which when covalently linked to the pharmacophores of the invention result in a decrease in kidney, spleen, gastrointestinal tract, and/or liver retention, thus enhancing the utility of pharmacophores for use with cytotoxic radioisotopes. In addition, the combination of the novel chelators of the invention with the novel pharmacophores disclosed herein results in high tumor uptake of the pharmacophore. The somatostatin analogs of the invention may be administered to treat somatostatin-responsive disease states, and in addition may be labeled with a radioisotope for use as diagnostic or therapeutic agents.

In one embodiment, the invention provides a compound comprising a somatostatin receptor-binding peptide having a formula cyclo-$B^1$-$B^2$-$B^3$-$B^4$-C-A wherein $B^1$ is Phe, Tyr, Nal, Ain, or a substituted derivative thereof;

$B^2$ is Trp or a substituted derivative thereof;

$B^3$ is Lys, Hly, Achxa, Amf, Aec, Apc, Aes, Aps or a substituted derivative thereof;

$B^4$ is Thr, Ser, Val, Phe, Ile, Abu, Nle, Leu, Nva, or Aib;

C is an L-α-amino acid;

A is an N-alkyl-α-amino acid or an N-substituted alkyl-α-amino acid, wherein A comprises a sidechain containing a sulfur atom;

wherein $B^1$ and A are covalently linked through an amino terminus of $B^1$ and a carboxyl terminus of A to form a cyclic peptide. In accordance with the invention, the A residue may be linked to a metal chelator through a sidechain nitrogen, carbon, sulfur, or oxygen atom. The compounds of the invention are characterized by molecular weights of less than about 10,000 daltons.

In another embodiment, the invention provides a compound comprising a somatostatin receptor-binding peptide having a formula

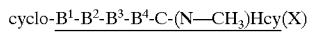

cyclo-$B^1$-$B^2$-$B^3$-$B^4$-C-(N—CH$_3$)Hcy(X)

wherein $B^1$ is Phe, Tyr, Nal, Ain, or a substituted derivative thereof;

$B^2$ is Trp or a substituted derivative thereof;

$B^3$ is Lys, Hly, Achxa, Amf, Aec, Apc, Aes, Aps or a substituted derivative thereof;

$B^4$ is Thr, Ser, Val, Phe, Ile, Abu, Nle, Leu, Nva, or Aib;

C is an L-α-amino acid;

X is a H or a metal chelator;

wherein $B^1$ and (N—CH$_3$)Hcy are covalently linked through an amino terminus of $B^1$ and a carboxyl terminus of (N—CH$_3$)Hcy to form a cyclic peptide. In accordance with the invention, X is linked to the (N—CH$_3$)Hcy residue through the Hcy sidechain sulfur atom.

In another embodiment, the invention provides a novel peptide chelator having a formula:

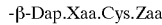

-β-Dap.Xaa.Cys.Zaa wherein

Xaa is an L-α-amino acid, and

Zaa is an α-amino acid, an α-amino acid amide, an aminoethylether, a β-aminol, or a peptide containing from two to ten α-amino acids, said peptide having a carboxyl terminal α-amino acid, α-amino acid amide, aminoethylether, or β-aminol.

In another embodiment, the invention provides a radiopharmaceutical comprising a compound of the invention and a radioisotope which may be a γ-emitter for imaging purposes, or alternatively, an α-emitter or a β-emitter for therapeutic purposes.

In another embodiment, the invention provides a kit comprising a sealed vial containing a predetermined quantity of a compound of the invention. The sealed vial may optionally contain a sufficient amount of a reducing agent to label the compound with $^{99m}$Tc, $^{186}$Re, or $^{188}$Re.

In yet another embodiment, the invention provides a method of imaging a site within a mammalian body, comprising the steps of radiolabeling a compound of the invention with a suitable γ-emitting radioisotope, administering an effective diagnostic amount of the radiolabeled compound to the body, and detecting the radioisotope accumulated at the site.

The invention also provides a method of treating an animal suffering a somatostatin-responsive disease, comprising the steps of radiolabeling a compound of the invention with an α-emitting or a β-emitting radioisotope, and administering a therapeutically effective amount of the radiolabeled compound to the animal.

The diagnostic and therapeutic methods of the invention may be combined to treat an SSTR-bearing tumor in a mammal, wherein a first aliquot of a compound of the invention is labeled with a γ-emitting radioisotope and used for diagnostic imaging, and if accumulation of the γ-emitting radioisotope is observed, a second aliquot of the same compound or a pharmacologically similar compound is labeled with a cytotoxic radioisotope and administered to the mammal to effect tumor ablation.

DETAILED DESCRIPTION OF THE INVENTION

The patent and scientific literature referenced herein establish the knowledge available to those with skill in the art. The issued U.S. patents and allowed applications are hereby incorporated by reference.

The novel pharmacophores of the invention bind with high affinity to SSTRs, and when covalently linked to the novel metal chelators of the invention, demonstrate high tumor uptake and, in addition, accumulate in liver, spleen, and/or kidney to a lower extent than known somatostatin analogs. The preferred compounds of the invention demonstrate improved properties such as subnanomolar affinity for SSTRs, high tumor uptake, and/or minimal kidney and/or gastrointestinal tract accumulation when radiolabeled.

The novel compounds of the invention may be used in unlabeled or labeled form to treat any somatostatin-responsive disease state. In general, somatostatin-responsive disease states are characterized by expression or over-expression of SSTRs. Exemplary somatostatin-responsive disease states include, without limitation, endocrine tumors such as those described supra, gastrointestinal tract tumors, breast carcinoma, small cell carcinoma of the lung, lymphoma, neuroblastoma, peptide hypersecretion from functional endocrine tumors of the gastroenteropancreatic axis, growth hormone hypersecretion in acromegaly, diabetic retinopathy, gut hypersecretion and increased motility in the dumping syndrome, pancreatic and gastrointestinal tract fistulas, complications following pancreatic surgery, increased portal pressure and variceal bleeding associated with esophageal varices, and the like.

As set forth above, the novel pharmacophore of the invention is embodied as a compound having the formula

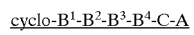

cyclo-$B^1$-$B^2$-$B^3$-$B^4$-C-A wherein $B^1$ is Phe, Tyr, Nal, Ain, or a substituted derivative thereof;

$B^2$ is Trp or a substituted derivative thereof;

$B^3$ is Lys, Hly, Achxa, Amf, Aec, Apc, Aes, Aps or a substituted derivative thereof;

$B^4$ is Thr, Ser, Val, Phe, Ile, Abu, Nle, Leu, Nva, or Aib;

C is an L-α-amino acid;

A is an N-alkyl-α-amino acid or an N-substituted alkyl-α-amino acid, wherein A comprises a sidechain containing a sulfur atom;

wherein $B^1$ and A are covalently linked through an amino terminus of $B^1$ and a carboxyl terminus of A to form a cyclic peptide. In the formula set forth above, "substituted" is intended to include such substitutions as H, amino, hydroxyl, N-alkyl wherein alkyl represents $C_1$ to $C_4$ alkyl, N,N-dialkyl wherein alkyl represents $C_1$ to $C_4$ alkyl, N-aryl, N-acyl, O-alkyl wherein alkyl represents $C_1$ to $C_4$ alkyl, O-aryl, O-acyl, S-alkyl wherein alkyl represents $C_1$ to $C_4$ alkyl, S-aryl, and the like. In accordance with the invention, the amino acids set forth above may be in the D- or L-configuration. As defined herein, "containing a sulfur atom" means that the sidechain of the A residue comprises such groups as —SH, —S—, —S—CH$_2$COOH, —S—CH$_2$COO—, —S—CH$_2$—CH(CO—)(NH—), and the like.

Preferably, B$^1$ is L-Phe or L-Tyr; B$^2$ is D-Trp; B$^3$ is L-Lys; and B$^4$ is L-Thr or L-Val, and A is an N-methyl-α-amino acid. More preferably, A is selected from the group consisting of (N—CH$_3$)Cys, (N—CH$_3$)Hcy, (N—CH$_3$)Tyr, (N—CH$_3$)Tty, and (N—CH$_3$)Tyr(CH$_2$CH$_2$SH). Most preferably, A is (N—CH$_3$)Tyr, (N—CH$_3$)Cys, or (N—CH$_3$)Hcy. When A is (N—CH$_3$)Tyr, (N—CH$_3$)Cys, or (N—CH$_3$)Hcy, C is preferably L -methionine, L -phenylalanine, or a substituted derivative of L-phenylalanine. More preferably, A is (N—CH$_3$)Cys or (N—CH$_3$)Hcy and C is L-phenylalanine or a substituted derivative of L-phenylalanine. Most preferably, A is (N—CH$_3$)Hcy and C is L-phenylalanine. In a most preferred embodiment, the pharmacophore of the invention has the formula:

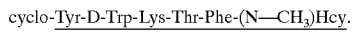

cyclo-Tyr-D-Trp-Lys-Thr-Phe-(N—CH$_3$)Hcy.

The use of the term "cyclo" and underlining of amino acids herein is intended to indicate that the peptide is cyclized by formation of an amide linkage between the substituted or unsubstituted amine group of the first underlined amino acid and the carboxyl group of the last underlined amino acid. Use of smaller font indicates that the chemical symbol for an atom is intended rather than a one-letter amino acid code.

All naturally-occurring amino acids may be referenced herein in abbreviated form, using standard one-letter or three-letter codes (which can be found in G. Zubay, *Biochemistry* (2d. ed.), 1988 (MacMillen Publishing: New York) p.33). In addition, as used herein, the following amino acids and amino acid analogues are intended to be represented by the following abbreviations: Hcy is homocysteine; Hhc is homohomocysteine (3-mercaptopropylglycine); Pen is penicillamine; Aib is aminoisobutyric acid; Nal is 2-naphthylalanine; Aca is 6-aminocaproic acid; Ain is 2-aminoindan-2-carboxylic acid; Hly is homolysine; Achxa is 4-amino-cyclohexylalanine; Amf is 4-aminomethyl-phenylalanine; Aec is S-(2-aminoethyl)cysteine; Apc is S-(3-aminopropyl) cysteine; Aes is O-(2-aminoethyl)serine; Aps is O-(3-aminopropyl)serine; Abu is 2-aminobutyric acid; Nva is norvaline; F$_D$ is D-phenylalanine; W$_D$ is D-tryptophan; Y$_D$ is D-tyrosine; Cpa is L-(4-chlorophenyl) alanine; Thp is 4-amino-tetrahydrothiopyran-4-carboxylic acid; D-Nal is D-2-naphthylalanine; Dpg is dipropylglycine; Nle is norleucine; (N—CH$_3$)Cys is N-methyl-cysteine; (N—CH$_3$)Hcy is N-methyl-homocysteine; (N—CH$_3$)Tyr is N-methyl-tyrosine; (N—CH$_3$)Tty is N-methyl-thiotyrosine (i.e., N-methyl-4-mercaptophenylalanine); (N—CH$_3$)Tyr (CH$_2$ $_{CH2\ SH}$) is N-methyl-O-2-mercaptoethyl tyrosine; Thr (OH) is threoninol residue (wherein the carboxyl group of the amino acid is reduced to a primary alcohol, incorporated into the peptide using the procedure of Neugebauer et al. (1990, *Peptides: Proceedings of the 11th American Peptide Symposium,* pp. 1020–21); Ser(ol) is. serinol; Asp(ol) is aspartinol; Glu(ol) is glutarinol; Gln(ol) is glutaminol; Asn (ol) is asparaginol; Phe(4-F) is 4-fluoro-phenylalanine; Phe (4-NH$_2$) is 4-amino-phenyalanine; ε-Lys represents a covalent linkage via the ε-amino group on the sidechain of a lysine residue; δ-Orn represents an ornithine residue in which the δ-amino group is covalently linked to the carboxyl group of the adjacent amino acid to form a peptide bond; γ-Dab represents a 2,4-diaminobutyric acid residue in which the γ-amino group is covalently linked to the carboxyl group of the adjacent amino acid to form a peptide bond; β-Dap represents a 2,3-diaminopropionic acid residue in which the β-amino group is covalently linked to the carboxyl group of the adjacent amino acid to form a peptide bond. When a combination of one-letter codes is used with the abbreviations set forth above, the abbreviation is set off by periods.

In accordance with the present invention, a "substituted derivative" of an amino acid includes such substitutions as amino, hydroxyl, N-alkyl wherein alkyl represents $C_1$ to $C_4$ alkyl, N-aryl, N-acyl, O-alkyl wherein alkyl represents $C_1$ to $C_4$ alkyl, O-aryl, O-acyl, S-alkyl wherein alkyl represents $C_1$ to $C_4$ alkyl, S-aryl. When applied to amino acids that contain a sidechain aromatic ring, the term also encompasses o-, m-, and p-substitutions including but not limited to o-amino, m-amino, p-amino, amino, o-hydroxyl, m-hydroxyl, p-hydroxyl, and the like.

The invention is also embodied as a compound having the formula:

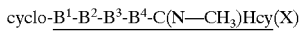

cyclo-B$^1$-B$^2$-B$^3$-B$^4$-C(N—CH$_3$)Hcy(X)

wherein B$^1$ is Phe, Tyr, Nal, Ain, or a substituted derivative thereof;

B$^2$ is Trp or a substituted derivative thereof;

B$^3$ is Lys, Hly, Achxa, Amf, Aec, Apc, Aes, Aps or a substituted derivative thereof;

B$^4$ is Thr, Ser, Val, Phe, Ile, Abu, Nle, Leu, Nva, or Aib;

C is L-methionine, L-phenylalanine, or a substituted derivative of L-phenylalanine;

X is H or a metal chelator;

wherein B$^1$ and (N—CH$_3$)Hcy are covalently linked through an amino terminus of B$^1$ and a carboxyl terminus of (N—CH$_3$)Hcy to form a cyclic peptide. In accordance with the invention, X is linked to the (N—CH$_3$)Hcy residue through the Hcy sidechain sulfur atom. The amino acids in the formula set forth above may be in the D- or L-configuration. In this embodiment, B$^1$ is preferably L-Phe or L-Tyr; B$^2$ is preferably D-Trp; B$^3$ is preferably L-Lys; and B$^4$ is preferably L-Thr or L-Val.

In accordance with the invention, any metal chelator may be employed as substituent X. For example, the compounds of the invention may comprise a metal ion chelator having a formula:

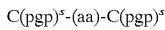

C(pgp)$^s$-(aa)-C(pgp)$^s$ where (pgp)$^s$ is hydrogen or a thiol protecting group and (aa) is any α- or β-amino acid not comprising a thiol group. In a preferred embodiment, the amino acid is glycine. Methods for making such a metal ion chelator are set forth in U.S. Pat. Nos. 5,654,272; 5,681,541; 5,788,960; and 5,811,394.

Alternatively, the compound of the invention may comprise a metal ion chelator capable of forming an electrically neutral complex with the metal ion, as set forth in U.S. Pat. Nos. 5,720,934; 5,776,428; 5,780,007; 5,922,303, 5,965, 107, 6,086,849 and 6,093,383. Such chelators include, but are not limited to

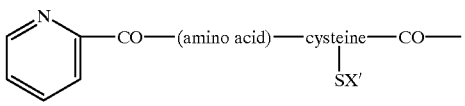

wherein
X'=H or a protecting group;
(amino acid)=any amino acid;

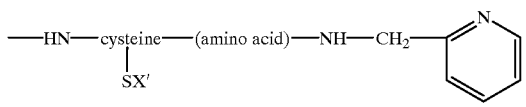

wherein
X'=H or a protecting group;
(amino acid)=any amino acid;

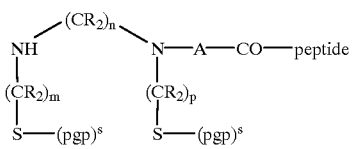

wherein each R is independently H, CH$_3$ or C$_2$H$_5$; each (pgp)$^s$ is independently a thiol protecting group or H; m, n and p are independently 2 or 3; A is linear C$_1$–C$_8$ alkyl, substituted linear C$_1$–C$_8$ alkyl, cyclic C$_3$–C$_8$ alkyl, substituted cyclic C$_3$–C$_8$ alkyl, aryl, substituted aryl, or a combination thereof; and

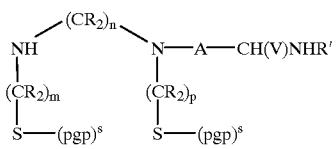

wherein each R is independently H, CH$_3$ or C$_2$H$_5$; m, n and p are independently 2 or 3; A is linear C$_1$–C$_8$ alkyl, substituted linear C$_1$–C$_8$ alkyl, cyclic C$_3$–C$_8$ alkyl, substituted cyclic C$_3$–C$_8$ alkyl, aryl, substituted aryl, or a combination thereof; V is H or CO-peptide; R' is H or peptide; provided that when V is H, R' is peptide and when R' is H, V is CO—pharmacophore. In accordance with the invention, the substituted derivatives in the bisamine, bisthiol formulae are defined as set forth above.

Alternatively, the compound of the invention may comprise a metal ion chelator having a formula selected from the group consisting of:

diethylenetriaminepentaacetic acid (DTPA);
a derivative of DTPA having a formula

where each R is independently H, C$_1$ to C$_4$ alkyl, or aryl and one R is covalently linked to a bivalent linker;

ethylenediaminetetraacetic acid (EDTA);
a derivative of EDTA having a formula

where each R is independently H, C$_1$ to C$_4$ alkyl, or aryl and one R is covalently linked to a bivalent linker;

1,4,7,10-tetraazacyclododecanetetraacetic acid and derivatives thereof such as those set forth in U.S. Pat. Nos. 4, 923,985; 5,053,503; 5,428,154; WO 94/27977, EP 512 661; and the like;

a metal ion chelator having a formula:

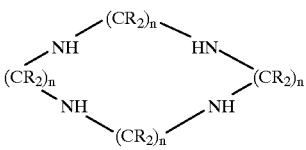

where n is an integer that is 2 or 3 and where each R is independently H, C$_1$ to C$_4$ alkyl, or aryl and one R is covalently linked to the peptide; and desferrioxamine.

In addition to the chelators set forth above, the somatostatin receptor-binding peptides of the invention may be covalently linked to radiometal binding ligand such as a hydrazino nicotinamide moiety and radiolabeled using appropriate co-ligands. Such ligands and co-ligands are disclosed, for example, in U.S. Pat. Nos. 5,300,278; 5,350, 837; 5,589,576; 5,679,778; and 5,879,659, and in Spies, et al. *Technetium, Rhenium and Other Metals in Chemistry and Nuclear Medicine,* Nicolini, et al., eds., SGEditoriali (Padua, 1999) pp. 101–108 and 687–690.

More preferably, the compounds of the invention comprise a monoamine, diamide, single thiol containing metal ion chelator such as those set forth in commonly assigned copending U.S. Ser. No. 08/253,973. Exemplary of such metal ion chelators are chelators having the formulae:

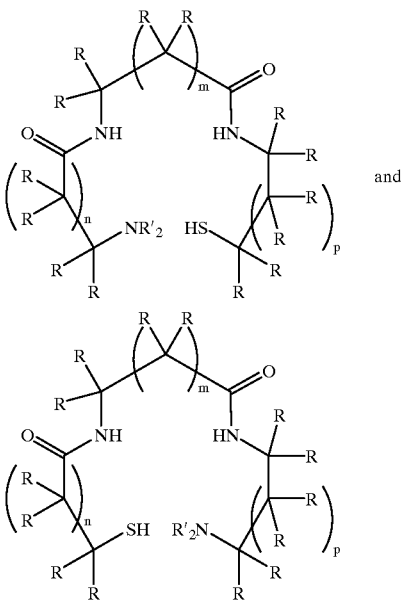

and wherein n, m and p are each integers that are independently 0 or 1; each R' is independently H, lower alkyl, C$_2$–C$_4$ hydroxyalkyl, or C$_2$–C$_4$ alkoxyalkyl, and each R is independently H or R", where R" is a substituted C$_1$–C$_8$ alkyl not comprising a thiol group, a unsubstituted C$_1$–C$_8$ alkyl, an unsubstituted phenyl, or a substituted phenyl not comprising a thiol group, and one R or R' is L$^2$, where L$^2$ is a bivalent linker moiety linking the metal chelator to the peptide and wherein when one R' is L$^2$, NR'$_2$ is an amine. In this embodiment, L$^2$ may be a C$_1$–C$_6$ linear alkyl group, a branched chain alkyl group, a cyclic alkyl group, a carboxylic ester, a carboxamide, a sulfonamide, an ether, a thioether, an amine, an alkene, an alkyne, a 1,2-linked, optionally substituted, benzene ring, a 1,3-linked, optionally substituted, benzene ring, a 1,4-linked, optionally substituted, benzene ring, or an amino acid, or a combination thereof In this embodiment, R" may be a $C_1$–$C_6$ linear alkyl group; a branched alkyl group; a cyclic alkyl group; a —$C_qOC_r$—, —$C_qNHC_r$— or —$C_qSC_r$— group, where q and r are integers each independently 1 to 5 wherein the sum of q+r is not greater than 6; ($C_1$–$C_6$) alkyl-X, where X is a hydroxyl group, a substituted amine, a guanidine, an amidine, a substituted thiol group, or a carboxylic acid, ester, phosphate, or sulfate group; a phenyl group or a phenyl group substituted with a halogen, a hydroxyl group, a substituted amine, a guanidine group, an amidine group, a substituted thiol, an ether, a phosphate, a sulfate; an indole group; a $C_1$–$C_6$ heterocyclic group containing 1 to 3 nitrogen, oxygen or sulfur atoms, or a combination thereof. In accordance with the invention, the substituted derivatives in the monoamine, diamide, thiol-containing chelator formulae are defined as set forth above.

Most preferably, the compounds of the invention comprise a metal ion chelator comprising a single thiol-containing group of formula:

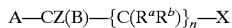

wherein A is H, HOOC—, $H_2NOC$—, —NHOC—, —OOC—, $R^e_2NOC$—, or $R^d$; B is H, SH, —$NHR^c$, $N(R^c)$— or $R^d$; Z is H or $R^d$; X is SH, —$NHR^c$, —$N(R^c)$— or $R^d$; $R^{a,\ Rb}$, $R^c$ and $R^d$ are independently H, straight chain $C_1$–$C_8$ alkyl, branched chain $C_1$–$C_8$ alkyl, or cyclic $C_3$–$C_8$ alkyl; n is 0, 1 or 2; $R^e$ is $C_1$–$C_4$ alkyl, an amino acid, or a peptide comprising 2 to about 10 amino acids; and: (1) where B is —$NHR^c$ or —$N(R^c)$—, X is SH and n is 1 or 2; (2) where X is —$NHR^c$ or —$N(R^c)$—, B is SH and n is 1 or 2; (3) where B is H or $R^d$, A is HOOC—, $H_2NOC$—, —NHOC—, or —OOC—, X is SH and n is 0 or 1; (4) where A is H or $R^d$, then where B is SH, X is —$NHR^c$ or —$N(R^c)$— and where X is SH, B is —$NHR^c$ or —$N(R^c)$— and n is 1 or 2; (5) where X is H or $R^d$, A is HOOC—, $H_2NOC$—, —NHOC—, or —OOC— and B is SH; (6) where Z is methyl, X is methyl, A is HOOC—, $H_2NOC$—, —NHOC—, or —OOC— and B is SH and n is 0; and (7) where B is SH, X is not SH and where X is SH, B is not SH.

In accordance with the invention, a metal ion chelator comprising a single thiol-containing group may have the formula:

$$R^1\text{—CO-(amino acid)}^1\text{-(amino acid)}^2\text{-}Z^1$$

wherein (amino acid)$^1$ and (amino acid)$^2$ are each independently any primary α- or β-amino acid that does not comprise a thiol group, $Z^1$ is selected from the group consisting of cysteine, homocysteine, isocysteine, penicillamine, 2-mercaptoethylamine, 2 -mercaptopropylamine, 2-mercapto-2-methylpropylamine, and 3-mercaptopropylamine, and $R^1$ is lower ($C^1$–$C^4$) alkyl, or $R^1$—CO is an amino acid, a peptide, or (aa)-peptide; wherein when $Z^1$ is cysteine, homocysteine, isocysteine or penicillamine, $Z^1$ comprises a carbonyl group covalently linked to a hydroxyl group, a $NR^3R^4$ group, wherein each of $R^3$ and $R^4$ are independently H, a bond, lower ($C^1$–$C^4$) alkyl, an amino acid or a peptide comprising from 2 to 10 amino acids.

Alternatively, a metal ion chelator comprising a single thiol-containing group may have the formula:

$$Y\text{-(amino acid)}^2\text{-(amino acid)}^1\text{-}NHR^2$$

wherein (amino acid)$^1$ and (amino acid)$^2$ are each independently any primary α- or β-amino acid that does not comprise a thiol group Y is selected from the group consisting of cysteine, homocysteine, isocysteine, penicillamine, 2-mercaptoacetate, 2-mercaptopropionate, 2-mercapto-2-methylpropionate, 3-mercaptopropionate, and $R^2$ is H, a bond, lower ($C^1$–$C^4$) alkyl, and $NHR^2$ is an amino acid, a peptide, or (aa)-peptide; wherein when Y is cysteine, homocysteine, isocysteine or penicillamine, Y comprises an amino group covalently linked to —H, an amino acid, a peptide, or (aa)-peptide.

For example, suitable metal ion chelators may have any of the following formulae:
(amino acid)$^1$-(amino acid)$^2$-cysteine-,
(amino acid)$^1$-(amino acid)$^2$-isocysteine-,
(amino acid)$^1$-(amino acid)$^2$-homocysteine-,
(amino acid)$^1$-(amino acid)$^2$-penicillamine-,
(amino acid)$^1$-(amino acid)$^2$-2-mercaptoethylamine-,
(amino acid)$^1$-(amino acid)$^2$-2-mercaptopropylamine-,
(amino acid)$^1$-(amino acid)$^2$-2-mercapto-2-methylpropylamine-,
(amino acid)$^1$-(amino acid)$^2$-3-mercaptopropylamine-,
wherein the chelator is attached to either a peptide or a linker group via a covalent bond with the carboxyl terminus of the chelator or a side chain on one of the amino acid groups.

Other suitable metal ion chelators include those selected from the group consisting of:
-cysteine-(amino acid)-(α,β- or β,γ-diamino acid);
-isocysteine-(amino acid)-(α,β- or β,γ-diamino acid);
-homocysteine-(amino acid)-(α,β- or β,γ-diamino acid);
-penicillamine-(amino acid)-(α,β- or β,γ-diamino acid);
2-mercaptoacetic acid-(amino acid)-(α,β- or β,γ-diamino acid);
2- or 3-mercaptopropionic acid-(amino acid)-(α,β- or β,γ-diamino acid);
2-mercapto-2-methylpropionic acid-(amino acid)-(α,β- or β,γ-diamino acid);
wherein the metal ion chelator is attached to either a peptide or a linker group via a covalent bond with the amino terminus of the chelator or a side chain on one of the amino acid groups.

Any naturally occurring, modified, substituted, or altered α- or β-amino acid not containing a thiol group may be used in the single-thiol chelators of the invention. As used herein, the term "modified, substituted, or altered α- or γ-amino acid" includes, without limitation, any of the amino acids identified above. Preferably, the α- or β-amino acid does not comprise more than sixteen carbon atoms.

The most preferred novel chelators of the invention have the formula:

wherein
 Xaa is an L-α-amino acid
 Zaa is an α-amino acid, an α-amino acid amide, an aminoethylether, a β-aminol, or a peptide containing from two to ten α-amino acids, said peptide having a carboxyl terminal α-amino acid, α-amino acid amide, aminoethylether, or β-aminol.

Homologs of β-Dap may also be employed in the novel chelators of the invention.

Suitable L-α-amino acids for substitution as Xaa in the novel chelator of the invention include naturally occurring amino acids such as asparagine, glutamine, threonine, serine, arginine, histidine, lysine, ornithine, phenylalanine, tyrosine, and, in addition, synthetic amino acids containing hydrophilic substituents. Exemplary synthetic amino acids include, without limitation, diaminopropionic acid; diaminobutyric acid; substituted tyrosines such as halotyrosine;

hydroxyltyrosine; aminotyrosine; substituted phenylalanines such as o-, m- or p-halophenylalanine; o-, m- or p-aminophenylalanine, wherein the amino substitutent may be a primary, secondary, or tertiary amine; o-, m- or p-hydroxylphenylalanine; o-, m- or p-O-alkylphenyalanine wherein alkyl represents $C_1$ to $C_4$ alkyl; o-, m- or p-O-acylphenylalanine; o-, m- or p-S-alkylphenylalanine wherein alkyl represents $C_1$ to $C_4$ alkyl; and the like In a preferred embodiment, Xaa is an L-α-amino acid such as serine, diaminobutyric acid, arginine, histidine, tyrosine, or a substituted phenylalanine. More preferably, Xaa is an aromatic an L-α-amino acid such as tyrosine, a substituted tyrosine residue such as iodotyrosine, bromotyrosine, chlorotyrosine, O-alkyl-tyrosine where alkyl represents $C_1$ to $C_8$ alkyl, hydroxyltyrosine, aminotyrosine, and the like, or a substituted phenylalanine residue. Most preferably, Xaa is a substituted phenylalanine residue wherein the substitutions include halogen, amino, hydroxyl, NH-alkyl wherein alkyl represents $C_1$ to $C_4$ alkyl, NH-acyl, O-alkyl wherein alkyl represents $C_1$ to $C_4$ alkyl, O-acyl, S-alkyl wherein alkyl represents $C_1$ to $C_4$ alkyl, SO-alkyl and $SO_2$-alkyl wherein alkyl represents $C_1$ to $C_4$ alkyl, $SO_3H$, $CO_2H$, $CO_2$-alkyl wherein alkyl represents $C_1$ to $C_4$ alkyl, CONH-alkyl wherein alkyl represents $C_1$ to $C_4$ alkyl. Specific embodiments of such substituted phenylalanine residues include 4-fluorophenylalanine, 4-chlorophenylalanine, 4-bromophenylalanine, 4-iodophenylalanine, 4-nitrophenylalanine, 4-aminophenylalanine, $N^4$-R-4-aminophenylalanine, $N^4$-R, $N^4$-R'-4-aminophenylalanine, or 3-R'-4-aminophenylalanine where R is $C_1$ to $C_4$ alkyl and R' is selected from the group consisting of H, $C_1$ to $C_4$alkyl amino, hydroxyl, NH-alkyl wherein alkyl represents $C_1$ to $C_4$ alkyl, NH-acyl, O-alkyl wherein alkyl represents $C_1$ to $C_4$ alkyl, O-acyl, S-alkyl wherein alkyl represents $C_1$ to $C_4$ alkyl, SO-alkyl and $SO_2$-alkyl wherein alkyl represents $C_1$ to $C_4$ alkyl, $SO_3H$, $CO_2H$, $CO_2$-alkyl wherein alkyl represents $C_1$ to $C_4$ alkyl, CONH-alkyl wherein alkyl represents $C_1$ to $C_4$ alkyl. The structures of exemplary most preferred substituted phenylalanine residues for use in the chelators of the invention are set forth below.

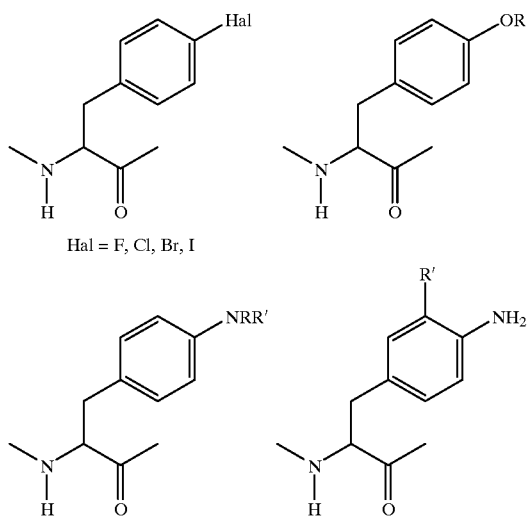

Hal = F, Cl, Br, I where R and R' are each independently H, a straight chain $C_1$ to $C_4$ alkyl group, a branched chain $C_1$ to $C_4$ alkyl group, or an aryl group. In accordance with the invention, the carboxyl terminal amino acid of the chelators of the invention may be in carboxylic acid form or in amidated form, or alternatively, in the form of a β-aminol.

The novel chelators of the invention have the properties of increasing the tumor uptake of the pharmacophore for SSTRs and enhancing kidney clearance of the radiolabeled peptide. Consequently, the novel chelators of the invention minimize retention of radiolabeled peptide in non-target tissues.

Specific embodiments of the compounds of the invention include the following peptides.

cyclo-Tyr-D-Trp-Lys-Thr-Phe-(N—CH$_3$)Hcy(CH$_2$ $_{CO}$-β-Dap-Tyr-Cys-Thr(ol))
cyclo-Tyr-D-Trp-Lys-Thr-Phe-(N—CH$_3$)Hcy(CH$_2$ $_{CO}$-β-Dap-Phe(4-F)-Cys-Thr(ol))
cyclo-Tyr-D-Trp-Lys-Thr-Phe-(N—CH$_3$)Hcy(CH$_2$ $_{CO}$-β-Dap-Phe(4-NH$_2$)-Cys-Thr-Ser)
cyclo-Tyr-D-Trp-Lys-Thr-Phe-(N—CH$_3$)Hcy(CH$_2$ $_{CO}$-β-Dap-Dab-Cys-Thr)
cyclo-Tyr-D-Trp-Lys-Thr-Phe-(N—CH$_3$)Hcy(CH$_2$ $_{CO}$-β-Dap-Phe(4-NH$_2$)-Cys-Thr)
cyclo-Tyr-D-Trp-Lys-Thr-Phe-(N—CH$_3$)Hcy(CH$_2$ $_{CO}$-β-Dap-Phe(4-NH$_2$)-Cys-Thr(ol))
cyclo-Tyr-D-Trp-Lys-Thr-Phe-(N—CH$_3$)Hcy(CH$_2$ $_{CO}$-β-Dap-His-Cys-Thr(ol))
cyclo-Tyr-D-Trp-Lys-Thr-Phe-(N—CH$_3$)Hcy(CH$_2$ $_{CO}$-β-Dap-Arg-Cys-Thr(ol))
cyclo-Tyr-D-Trp-Lys-Thr-Phe-(N—CH$_3$)Hcy(CH$_2$ $_{CO}$-β-Dap-Gly-Cys-Lys-NH$_2$)
cyclo-Tyr-D-Trp-Lys-Thr-Phe-(N—CH$_3$)Hcy(CH$_2$ $_{CO}$-β-Dap-Ser-Cys-Thr(ol))
cyclo-Tyr-D-Trp-Lys-Thr-Phe-(N—CH$_3$)Hcy(CH$_2$ $_{CO}$-β-Dap-Dab-Cys-Thr(ol))
cyclo-Tyr-D-Trp-Lys-Thr-Phe-(N—CH$_3$)Hcy(CH$_2$ $_{CO}$-β-Dap-Gly-Cys-Thr(ol))
cyclo-Tyr-D-Try-Lys-Thr-Phe-(N—CH$_3$)Hcy(CH$_2$ $_{CO}$-β-Dap-Dab-Cys-Ser(ol))
cyclo-Tyr-D-Trp-Lys-Thr-Phe-(N—CH$_3$)Hcy(CH$_2$ $_{CO}$-Gly-Gly-Cys-Lys-NH$_2$)
cyclo-Tyr-D-Trp-Lys-Thr-Phe-(N—CH$_3$)Hcy(CH$_2$ $_{CO}$-Gly-Gly-Cys-Arg-NH$_2$)
cyclo-Tyr-D-Trp-Lys-Thr-Phe-(N—CH$_3$)Hcy(CH$_2$ $_{CO}$-Ser-Ser-Cys-Lys-NH$_2$)
cyclo-Tyr-D-Trp-Lys-Thr-Phe-(N—CH$_3$)Hcy(CH$_2$ $_{CO}$-Ser-Ser-Cys-Arg-NH$_2$)
cyclo-Tyr-D-Trp-Lys-Thr-Phe-(N—CH$_3$)Hcy(CH$_2$ $_{CO}$-Ser-Ser-Cys-Lys-Thr(ol))
cyclo-Tyr-D-Trp-Lys-Thr-Phe-(N—CH$_3$)Hcy(CH$_2$ $_{CO}$-Ser-Ser-Cys-Dap-NH$_2$)
cyclo-Tyr-D-Trp-Lys-Thr-Phe-(N—CH$_3$)Hcy(CH$_2$ $_{CO}$-Ser-Ser-Cys-NH(CH$_2$ $_{CH2\ O}$)$_2$ $_{CH2\ CH2\ NH2}$)
cyclo-Tyr-D-Trp-Lys-Thr-Phe-(N—CH$_3$)Hcy(CH$_2$ $_{CO}$-β-Dap-Ser-Cys-Thr-NH(CH$_2$ $_{CH2\ O}$)$_2$ $_{CH2\ CH2\ NH2}$)
cyclo-Tyr-D-Trp-Lys-Thr-Phe-(N—CH$_3$)Hcy(CH$_2$ $_{CO}$-Gly-Lys-Cys-NH$_2$)
cyclo-Tyr-D-Trp-Lys-Thr-Phe-(N—CH$_3$)Hcy(CH$_2$ $_{CO}$-Ser-Lys-Cys-NH$_2$)
cyclo-Tyr-D-Trp-Lys-Thr-Phe-(N—CH$_3$)Hcy(CH$_2$ $_{CO}$-Lys-Gly-Cys-NH$_2$)
cyclo-Tyr-D-Trp-Lys-Thr-Phe-(N—CH$_3$)Hcy(CH$_2$ $_{CO}$-Ser-Dab-Cys-Ser(ol))
cyclo-Tyr-D-Trp-Lys-Thr-Phe-(N—CH$_3$)Hcy(CH$_2$ $_{CO}$-Ser-Dap-Cys-NH$_2$)
cyclo-Tyr-D-Trp-Lys-Thr-Phe-(N—CH$_3$)Hcy(CH$_2$ $_{CO}$-Gly-Gly-Cys-His-NH$_2$)
cyclo-Tyr-D-Trp-Lys-Thr-Phe-(N—CH$_3$)Hcy(CH$_2$ $_{CO}$-Gly-Gly-Cys-Phe(4 NH$_2$)-NH$_2$)
cyclo-Tyr-D-Trp-Lys-Thr-Phe-(N—CH$_3$)Hcy(CH$_2$ $_{CO}$-β-Dap-Orn-Cys-Thr(ol))
cyclo-Tyr-D-Trp-Les-Thr-Phe-(N—CH$_3$)Hcy(CH$_2$ $_{CO}$-β-Dap-Dap-Cys-Thr(ol))

cyclo-Tyr-D-Trp-Lys-Thr-Phe-(N—CH$_3$)Hcy(CH$_2$ $_{CO}$-β-Dap-Lys-Cys-Thr(ol))

cyclo-Tyr-D-Trp-Lys-Thr-Phe-(N—CH$_3$)Hcy(CH$_2$ $_{CO}$-Ser-Ser-Cys-NHCH$_2$ $_{CH2\ OCH2\ CH2\ NH2}$)

cyclo-Tyr-D-Trp-Lys-Thr-Phe-(N—CH$_3$)Hcy(CH$_2$ $_{CO}$-β-Dap-Lys-Cys-NH$_2$)

cyclo-<u>Tyr-D-Trp-Lys-Thr-Phe</u>-(N—CH$_3$)Hcy(CH$_2$ $_{CO}$-δ-Orn-Gly-Cys-NH$_2$)

cyclo-<u>Tyr-D-Trp-Lys-Thr-Phe</u>-(N—CH$_3$)Hcy(CH$_2$ $_{CO}$-Thr-Gly-Gly-Cys-NH$_2$)

Preferred compounds of the invention exhibit high affinity for SSTRs, as indicated in Example 5. In accordance with the invention, high affinity for SSTRs is defined as less than about 25 nanomolar affinity for SSTRs as measured in a SSTR binding affinity assay such as the assay set forth in Example 5. More preferred compounds of the invention are characterized by high affinity for SSTRs, as indicated in Example 5, and by high tumor uptake, as indicated in Example 6. As defined herein, high tumor uptake means a percent injected dose (% ID) of $^{99m}$Tc per gram tumor (% ID/g), in the nude mouse/rat AR42J xenograft model described in Example 6, of greater than about 4. Most preferred embodiments of the compounds of the invention have a tumor uptake greater than about 15% ID/g and a kidney uptake less than about 7% ID/g to about 9% ID/g; or alternatively a tumor uptake greater than about 10% ID/g, a kidney uptake less than about 7% ID/g to about 9% ID/g, and a gastrointestinal tract uptake less than about 5% ID/g to about 7% ID/g. Exemplary most preferred compounds of the invention include:

cyclo-Tyr-D-Trp-Lys-Thr-Phe-(N—CH$_3$)Hcy(CH$_2$ $_{CO}$-β-Dap-Tyr-Cys-Thr(ol))

cyclo-Tyr-D-Trp-Lys-Thr-Phe-(N—CH$_3$)Hcy(CH$_2$ $_{CO}$-β-Dap-Phe(4-F)-Cys-Thr(ol))

cyclo-Tyr-D-Trp-Lys-Thr-Phe-(N—CH$_3$)Hcy(CH$_2$ $_{CO}$-β-Dap-Phe(4-NH$_2$)-Cys-Thr-Ser)

cyclo-Tyr-D-Trp-Lys-Thr-Phe-(N—CH$_3$)Hcy(CH$_2$ $_{CO}$-β-Dap-Phe(4-NH$_2$)-Cys-Thr(ol))

cyclo-Tyr-D-Trp-Lys-Thr-Phe-(N—CH$_3$)Hcy(CH$_2$ $_{CO}$-β-Dap-Dab-Cys-Thr(ol))

Methods for making the compounds of the invention, and in particular those comprising the metal ion chelators of the most preferred embodiment are set forth in U.S. Pat. Nos. 5,443,815; 5,807,537; 5,814,297; 5,866,097, 5,997,844 and 6,074,627; and in U.S. Ser. Nos. 08/236,402; 08/253,973. As disclosed therein, the compounds of the invention may be made using a commercially available peptide synthesizer. Example 1 sets forth an exemplary method of making an embodiment of the pharmacophore of the present invention. Other embodiments of the novel pharmacophore are made using similar methods. Example 2 sets forth an exemplary method of making an embodiment of the novel chelator of the invention.

In accordance with the invention, the A residue may be linked to a metal chelator through a sidechain nitrogen, sulfur, or oxygen atom of the A residue. Linkage may be direct or through intervening atoms or amino acid residues. In a preferred embodiment, the linkage is through —CH$_2$CO—. Such linkages may be accomplished via the alkylation of these atoms with moieties containing reactive electrophiles such as alkyl halides. These atoms may also be reacted with chelators containing isocyanates, isothiocyanates, or activated carboxylic esters. An appropriately protected A residue may also be linked to a metal chelator through a sidechain carbon by forming a Wittig or Emmons-Homer reagent on the sidechain and reacting this with an aldehydo functionality on an appropriately protected chelator. The resulting double bond linkage can be left as is or subsequently reduced to yield saturated hydrocarbon linkage. Example 3 sets forth an exemplary method of attaching a chelator through a sidechain sulfur atom of an (N—CH$_3$)Hcy residue of the pharmacophore.

Those of skill will recognize that most metal ions may be chelated to the above-mentioned metal ion chelators and ligand/coligand radiometal binding moieties. Any metal ion capable of generating a signal may be chelated to the pharmacophore of the invention, thus forming a metal ion complex with the compound of the invention. Suitable metal ions include radioactive metal ions, fluorescent metal ions, paramagnetic metal ions, heavy metals, rare earth ions suitable for use in computerized tomography, and the like. Radioactive metal ions or radionuclides are preferred. More preferably, γ-emitting radionuclides such as $^{67}$Cu, $^{67}$Ga, $^{111}$In, and $^{99m}$Tc; β-emitting radionuclides such as $^{90}$y, $^{186}$Re, or $^{166}$Ho; β/γ emitting radionuclides such as $^{67}$Cu, $^{47}$Sc, $^{153}$Sm, or $^{188}$Re; positron-emitting radionuclides such as $^{68}$Ga, $^{94m}$Tc, $^{64}$Cu, or α-emitting radionuclides such as $^{213}$Bi, $^{212}$Bi, $^{225}$Ac, $^{223}$Ra are used in the methods of the invention. Most preferably, $^{99m}$Tc, $^{188}$Re and/or $^{186}$Re are used in the methods of the invention.

Those of skill will recognize that the pharmacophores and compounds of the invention may be labeled with radioisotopes of halogens, such as $^{125}$I $^{131}$I, $^{123}$I, $^{18}$F, and $^{211}$At, through a tyrosine residue which may be added to the pharmacophore or to the compound using known methods, or using other known methods such as Bolton-Hunter reagent, chloramine T, and the like.

The compounds of the invention may also be complexed with non-radioactive metals, such as rhenium, using methods similar to those set forth below. Table 4 indicates that compounds of the invention effectively inhibit binding of $^{125}$I-Tyr$^{11}$-somatostatin-14 when complexed with rhenium.

Complexes of the invention may be formed using known methods. For example, a salt of $^{98m}$Tc pertechnetate, $^{188}$Re perrhenate, or $^{186}$Re perrhenate may be reacted with the compound in the presence of a reducing agent such as dithionite ion, stannous ion, or ferrous ion. In this method, the most preferred reducing agent is stannous chloride. Alternatively, complexes and chelates may be formed by ligand exchange, wherein the compound of the invention is reacted with a pre-formed labile complex of $^{99m}$Tc, $^{188}$Re, or $^{186}$Re and another compound known as a transfer ligand. In this process, any transfer ligand may be used, for example, tartrate, citrate, gluconate, glucoheptonate, mannitol, and the like. Exemplary methods for labeling the compounds of the invention with $^{99m}$Tc and $^{188}$Re are set forth in Example 4. In general, an appropriate quantity of a reagent of the invention is introduced into a vial containing a reducing agent, such as stannous chloride, in an amount sufficient to label the reagent with $^{99m}$Tc, $^{188}$Re, or $^{186}$Re. Generally, more reducing agent is required to effect labeling with $^{188}$Re or $^{186}$Re than is required to effect labeling with $^{99m}$Tc.

The compounds of the invention may be supplied in the form of a pyrogen-free, parenterally acceptable pharmaceutical composition, which may be an aqueous solution or a lyophilizate for reconstitution. The preparation of such pharmaceutical compositions, having due regard to pH, isotonicity, stability, and the like, is within the skill in the art. The pharmaceutical composition of the invention may include pharmaceutically acceptable diluents, such as, for example, Sodium Chloride Injection and Ringer's Injection. For administration to humans, the composition may be administered in autologous serum or plasma. Supplementary active compounds may also be co-administered with the somatostatin analog, in accordance with the invention.

The pharmaceutical compositions of the invention may optionally contain a stabilizer such as gentisic acid as set forth in U.S. Pat. Nos. 4,232,000; 4,233,284; 4,497,744; 5,384,113, and/or ascorbic acid as disclosed in U.S. Pat. Nos. 5,393,512 and 5,011,676, in WO 97/28181 and in WO 98/33531. Alternatively, hydroquinone stabilizers such as those disclosed in U.S. Pat. No. 4,229,427 may be added to the complexes of the invention. Other compounds such as reductic acid, erythorbic acid, p-aminobenzoic acid, 4-hydroxybenzoic acid, nicotinic acid, nicotinamide, 2,5-dihydroxy-1,4-benzenedisulfonic acid, tartaric acid, inositol, and the like, may also be added to stabilize the complexes of the invention.

The invention is also embodied in a kit for preparing radiometal-labeled reagents for use as radiopharmaceuticals. The kit of the invention comprises a sealed vial containing a predetermined quantity of the compound of the invention, and optionally, when the radiometal is $^{99m}$Tc, $^{188}$Re, or $^{186}$Re, a reducing agent. Stabilizers such as gentisic acid and/or ascorbic acid or any of the stabilizers described above may also be included in kits intended for $^{188}$Re or $^{186}$Re radiolabeling. An appropriate amount of a transfer ligand as described above (such as tartrate, citrate, gluconate, glucoheptanate or mannitol, for example) can also be included in the kit. The kit may also contain conventional pharmaceutical adjunct materials such as, for example, pharmaceutically acceptable salts to adjust the osmotic pressure, buffers, preservatives, additional vials, and the like. The kit may also contain instructions for radiolabeling. The components of the kit may be in liquid, frozen or dry form. In a preferred embodiment, kit components are provided in lyophilized form.

The kit of the invention may also be embodied in a form suitable for diagnostic imaging or as a therapeutic agent using a radioisotope of a halogen, including $^{18}$F, $^{211}$At, $^{125}$I and $^{131}$I, and preferably $^{123}$I. In this embodiment, the kit comprises a sealed vial containing a predetermined quantity of a compound of the invention which may be modified to a form capable of being radiolabeled with an iodine isotope, using known methods as described above. Dose, sites and routes of administration, formulations and administered specific radioactivity using the kit of this embodiment are as described herein for technetium and rhenium-labeled reagents for scintigraphic and therapeutic uses.

The compounds of the invention may be used in radiolabeled or unlabeled form to diagnose or treat any somatostatin-responsive disease state. The compounds of the invention are particularly useful for diagnosis and/or treatment of tumors such as neuroendocrine tumors, for example, pituitary adenomas, pheochromocytomas, paragangliomas, medullary thyroid carcinomas, small cell and non small cell lung cancers, astrocytomas, melanomas, meningiomas, breast tumors, malignant lymphomas, renal cell carcinomas, prostate tumors, and the like. The compounds of the invention may also be used to diagnose or to treat conditions in which angiogenesis and concomitant upregulation of SSTRs occurs, as described in Woltering, et al., supra. As set forth in commonly assigned allowed U.S. Ser. No. 08/976,995, the compounds of the invention are useful in imaging and treating conditions of high cellular proliferation in the cardiovascular system. Such conditions include, for example, atherosclerosis and cellular proliferation occurring in arteries after invasive procedures such as angioplasty.

Preferably, radiolabeled complexes of the compounds of the invention are used for such diagnoses and treatments. Radiolabeled embodiments of the compounds of the invention may be used in radioisotope guided surgery, as described in WO 93/18797 and in Woltering, et al. (1994) *Surgery* 116, 1139–1147. In a preferred embodiment, a complex of a γ-emitting radionuclide such as $^{99m}$Tc and a compound of the invention is used to diagnose an SSTR-expressing tumor, and subsequently, a complex of β-emitting radionuclide such as $^{188}$Re or $^{186}$Re with the compound is used to treat the tumor.

For diagnostic purposes, an effective diagnostic amount of the diagnostic or radiodiagnostic agent of the invention is administered, preferably intravenously. An effective diagnostic amount is defined as the amount of diagnostic or radiodiagnostic agent necessary to effect localization and detection of the label in vivo using conventional methodologies such as magnetic resonance, computerized tomography, gamma scintigraphy, SPECT, PET, and the like.

For diagnosis using scintigraphic imaging, preferably, $^{99m}$Tc-labeled compounds of the invention are administered in a single unit injectable dose. The $^{99m}$Tc-labeled compounds provided by the invention may be administered intravenously in any conventional medium for intravenous injection such as an aqueous saline medium, or in blood plasma medium. Generally, the unit dose to be administered has a radioactivity of about 0.01 mCi to about 100 mCi, preferably 1 mCi to 50 mCi. The solution to be injected at unit dosage is from about 0.01 mnL to about 10 mL. After intravenous administration, imaging in vivo can take place in a matter of a few minutes. However, imaging can take place, if desired, hours or even longer after the radiolabeled compound is injected into a patient. In most instances, a sufficient amount of the administered dose will accumulate in the area to be imaged within about 0.1 of an hour to permit the taking of scintiphotos. Any conventional method of scintigraphic imaging for diagnostic purposes can be utilized in accordance with this invention.

When the radiolabeled compounds of the invention are used for therapeutic purposes, they are radiolabeled with a therapeutically effective amount of a cytotoxic radioisotope, preferably $^{188}$Re. In accordance with the invention, a therapeutically effective amount of a cytotoxic radioisotope means the total amount of each active component of the pharmaceutical composition or method that is sufficient to show a meaningful patient benefit, i.e., a reduction in the incidence or severity of symptoms attributed to the somatostatin-responsive disease state, as compared to that expected for a comparable group of patients not receiving the radiotherapeutic agent of the invention. When applied to an individual active ingredient administered alone, the term refers to that ingredient alone. When applied to a combination, the term refers to combined amounts of the active ingredients that result in the therapeutic effect, whether administered in combination, serially, or simultaneously. For the purposes of this invention, radiotherapy encompasses any therapeutic effect ranging from pain palliation to tumor ablation or remission of symptoms associated with the particular somatostatin-responsive disease being treated.

When used for radiotherapy, a complex of the compound of the invention and a cytotoxic radioisotope is administered to a mammal, including a human patient, in need of treatment for a somatostatin-responsive disease. In the radiotherapeutic method of the invention, an amount of cytotoxic radioisotope from about 5 mCi to about 200 mCi may be administered via any suitable clinical route, preferably by intravenous injection or by intratumoral injection. The radiotherapeutic complex of the invention may optionally be administered in combination with a chemotherapeutic drug such as tamoxifen, cisplatin, taxol, anti-angiogenic compounds, and the like.

When unlabeled compound is used for therapy of a somatostatin-responsive disease state, administration of the compound is preferably parenteral, and more preferably intravenous. The amount of unlabeled compound administered for therapy of a somatostatin-responsive disease will depend upon the nature and severity of the condition being treated, and upon the nature of prior treatments which the patient has undergone. Ultimately, the attending physician will decide the amount of compound with which to treat each individual patient. Initially, the attending physician will administer low doses of the compound and observe the patient's response. Larger doses of the compound may be administered until the optimal therapeutic effect is obtained for the patient, and at that point the dosage is not increased further. It is contemplated that the dosage of unlabeled compound administered in the therapeutic method of the invention should be in the range of about 0.1 μg to about 100 mg compound per kg body weight. More preferably, the dosage of unlabeled compound administered in the therapeutic method of the invention is in the range of about 0.1 μg to about 100 μg compound per kg body weight. The unlabeled compound of the invention may also optionally be administered in combination with a chemotherapeutic drug.

The duration of therapy, whether with a radiopharmaceutical comprising a compound of the invention or with an unlabeled compound of the invention, will vary, depending on the severity of the disease being treated and the condition and idiosyncratic response of each individual patient. It is contemplated that the duration of each administration of the radiopharmaceutical of the invention will be in the range of about one to about 120 minutes of continuous intravenous administration. It is contemplated that the duration of each administration of the unlabeled compound of the invention will be in the range of about one to about 120 minutes of continuous intravenous administration. Ultimately the attending physician will decide on the appropriate duration of intravenous therapy using the labeled or unlabeled compounds of the invention, whether administered alone or in combination with other drugs.

The following examples are shown by way of illustration and not by way of limitation.

EXAMPLE 1

Solid-Phase Synthesis of Protected Pharmacophore

Step 1. Fmoc-Lys(Boc)-Thr(tBu)-ClTrt Resin. 2-chlorotrityl resin-supported O-t-butyl-threonine (2.5 g, 1.1 mmol/g, 2.75 mmol) was placed in peptide synthesis vessel and washed twice for 5 minutes with 30 mL N-methylpyrolidinone (NMP) with gentle agitation of the resin by argon gas. A small aliquot of resin was removed for ninhydrin analysis (as a control) and the resin washed with NMP (30 mL×1 min). In a separate flask, N-α-Fmoc-N-ε-Boc-lysine (3.22 g, 6.88 mmol) and 2-{O-(7-azabenzotriazol-1-yl}-1,1,3,3-tetramethyluronium hexafluorophosphate (HATU reagent) (2.56 g, 6.74 mmol) were dissolved in 30 mnL of NMP. N,N-diisopropylethylamine (DIEA: 2.40 mL, 13.76 mmol) was added to the protected lysine solution. The flask was swirled for 1 minute and the contents added to the peptide synthesis vessel containing the resin-supported amino acid. The resin was agitated with a gentle stream of argon for 2.0 hrs. The solution was drained and the resin washed sequentially with NMP (3×30 mL×1 min) and dichloromethane (DCM: 3×30 mL×1 min). Ninhydrin analysis performed on a small portion of resin indicated that the reaction was complete.

Step 2. Fmoc-D-Trp(Boc)-Lys(Boc)-Thr(tBu)-ClTrt Resin. The resin-supported peptide from Step 1 was treated with 5% piperidine in 1:1 NMP/DCM (30 mL) for 10 minutes followed by treatment with 20% piperidine in NMP (30 mL) for 15 minutes. The resin was sequentially washed with NMP (3×30 mL×1 min) and DCM (3×30 mL×1 min). A small aliquot of resin was removed for ninhydrin analysis (as a control) and the resin washed with NMP (30 mL). In a separate flask, N-α-Fmoc-N-in-Boc-D-tryptophan (3.62 g, 6.88 mmol) and HATU reagent (2.56 g, 6.74 mmol) were dissolved in 30 mL of NMP. DIEA (2.40 mL, 13.76 mmol) was added to the protected tryptophan solution. The flask was swirled for 1 minute and the contents added to the peptide synthesis vessel containing the resin-supported peptide. The resin was agitated with a gentle stream of argon for 2.0 hrs. The solution was drained and the resin washed sequentially with NMP (3×30 mL×1 min) and DCM (3×30 mL×1 min). Ninhydrin analysis performed on a small portion of resin indicated that the reaction was complete.

Step 3. Fmoc-Tyr(tBu)-D-Trp(Boc)-Lys(Boc)-Thr(tBu)-ClTrt Resin. The resin-supported peptide from Step 2 was treated with 5% piperidine in 1:1 NMP/DCM (30 mL) for 10 minutes followed by treatment with 20% piperidine in NMP (30 mL) for 15 minutes. The resin was sequentially washed with NMP (3×30 mL×1 min) and DCM (3×30 mL×1 min). A small aliquot of resin was removed for ninhydrin analysis (as a control) and the resin washed with NMP (30 mL). In a separate flask, N-α-Fmoc—O-t-butyl-tyrosine (3.16 g, 6.88 mmol) and HATU reagent (2.56 g, 6.74 mmol) were dissolved in 30 mL of NMP. DIEA (2.40 mL, 13.76 mmol) was added to the protected tyrosine solution. The flask was swirled for 1 minute and the contents added to the peptide synthesis vessel containing the resin-supported peptide. The resin was agitated with a gentle stream of argon for 2.0 hrs. The solution was drained and the resin washed sequentially with NMP (3×30 mL×1 min) and DCM (3×30 mL×1 min). Ninhydrin analysis performed on a small portion of resin indicated that the reaction was complete.

Step 4. H-Hcy(Trt)-Tyr(tBu)-D-Trp(Boc)-Lys(Boc)-Thr(tBu)-ClTrt Resin. The resin-supported peptide was treated with 5% piperidine in 1:1 NMP/DCM (30 mL) for 10 minutes followed by treatment with 20% piperidine in NMP (30 mL) for 15 minutes. The resin was sequentially washed with NMP (3×30 mL×1 min) and DCM (3×30 mL×1 min). A small aliquot of resin was removed for ninhydrin analysis (as a control) and the resin washed with NMP (30 mL). In a separate flask, N-α-Fmoc-S-trityl-homocysteine (3.16 g, 6.88 mmol) and HATU reagent (2.56 g, 6.74 mmol) were dissolved in 30 mL of NMP. DIEA (2.40 mL, 13.76 mmol) was added to the protected homocysteine solution. The flask was swirled for 1 minute and the contents added to the peptide synthesis vessel containing the resin-supported peptide. The resin was agitated with a gentle stream of argon for 2.0 hrs. The solution was drained and the resin washed sequentially with NMP (3×30 mL×1 min) and DCM (3×30 mL×1 min). Ninhydrin analysis performed on a small portion of resin indicated that the reaction was complete. The resin was treated with 5% piperidine in 1:1 NMP/DCM (30 mL) for 10 minutes followed by treatment with 20% piperidine in NMP (30 mL) for 15 minutes. The resin was sequentially washed with NMP (3×30 mL×1 min) and DCM (3×30 mL×1 min). A small aliquot of resin was removed for ninhydrin analysis (as a control). A small portion of resin was also removed for HPLC analysis which was performed as follows: the resin portion (~1–3 mg) was treated with 250

μL of 1:4 1,1,1,3,3,3-hexafluoro-2-propanol (HFIPA)/DCM for 5 min. An aliquot (15 μL) of the cleavage mixture was diluted with 150 μL of 0.1% (v/v) TFA in 9:1 (v/v) acetonitrile/water. The solution was analyzed by C18 reversed-phase analytical HPLC as outlined in HPLC Method 1.

| HPLC Method 1: | |
|---|---|
| Column: | Vydac C18, 4.6 mm × 150 mm |
| Solvent A: | 0.1% (v/v) TFA in water |
| Solvent B: | 0.1% (v/v) TFA in 9:1 (v/v) acetonitrile/water |
| Gradient: | 50%–100% B/A over 20 min, 100% B over 5 min |
| Flow Rate: | 1.2 mL/min |
| Injection Volume: | 10 μL |
| Detection: | UV (220 nm) |

The chromatogram resulting from the HPLC analysis of the cleaved protected peptide exhibited only one peak with a retention time of 18.7 minutes.

Step 5. 2-NO$_2$—Ph SO$_2$—Hcy(Trt)-Tyr(tBu)-D-Trp(Boc)-Lys(Boc)-Thr(tBu)-ClTrt Resin. The resin-supported peptide from Step 4 was washed with anhydrous DCM (30 mL×1 min), suspended in anhydrous DCM (30 mL×1 min), and treated with 2,4,6-collidine (1.82 mL, 13.8 mmol). 2—Nitrobenzenesulfonyl chloride (1.52 g, 6.9 mmol) in 20 mL of DCM was added and the reaction gently agitated with argon gas for 14 hours. The reaction solution was drained and the resin washed with DCM (2×30 mL×1 min), NMP (2×30 mL×1 min) and DCM (3×30 mL×1 min). A small sample of resin was removed, treated with HFIPA, and analyzed by HPLC as before (HPLC Method 1). The peak of peptide free N-terminal amine at 18.7 minutes was absent and was replaced by a peak at 21.6 minutes, representing the sulfonated peptide.

Step 6. H—(N—CH$_3$)Hcy(Trt)-Tyr(tBu)-D-Trp(Boc)-Lys(Boc)-Thr(tBu)-ClTrt Resin. The resin-supported peptide was washed with NMP (2×30 mL×1 min), anhydrous DMF (1×30 mL×1 min), and transferred with the aid of 40 mL of anhydrous DMF to a dry 100 mL round bottom flask equipped with a stir bar. 1,3,4,6,7,8-hexahydro-1-methyl-2H-pyrimido{1,2-a}pyrimidine (MTBD, 0.79 mL, 5.5 mmol) was added and the resin suspension was stirred for 15 minutes (green color) under an atmosphere of argon. The resin was treated with iodomethane (0.26 mL, 4.13 mmol) and stirred for 5 hours under an atmosphere of argon. The suspension was transferred back to the peptide synthesis vessel and the reaction solution was drained off. The resin was washed with NMP (3×30 mL×1 min) and DCM (3×30 mL×1 min). A small sample of resin was removed, treated with 1:4 HFIPA/DCM, and the progress of the reaction was monitored by HPLC as before (HPLC Method 1). This chromatogram resulting from this HPLC analysis indicated that the reaction was >90% complete, with the N-methylated peptide exhibiting a retention time of 22.1 minutes. The resin was treated with NMP (30 mL) containing 2-mercaptoethanol (BME, 0.58 mL, 8.25 mmol) and 1,8-diazabicyclo{5.4.0}undec-7-ene (DBU, 1.23 mL, 8.25 mmol) for 15 minutes. The solution was drained and the resin washed with NMP (3×30 mL×1 min) and DCM (3×30 mL×1 min). A small sample of resin was removed, treated with 1:4 HFIPA/DCM, and the progress of the reaction was monitored by HPLC as before (HPLC Method 1). The chromatogram resulting from this HPLC analysis indicated that removal of the sulfonyl group was >90% complete with the desulfonated peptide exhibiting a retention time of 18.5 minutes.

Step 7. H-Phe-(N—CH$_3$)Hcy(Trt)-Tyr(tBu)-D-Trp(Boc)-Lys(Boc)-Thr(tBu)-OH. N-Fmoc-phenylalanine (3.20 g, 8.25 mmol) and HATU reagent (3.14 g, 8.25 mmol) were dissolved in 30 mL of NMP. DIEA (2.40 mL, 13.76 mmol) was added to the protected phenylalanine solution. The flask was swirled for 1 minute and the contents added to the peptide synthesis vessel containing the resin-supported peptide. The resin was agitated with a gentle stream of argon for 5 hrs. The solution was drained and the resin washed sequentially with NMP (3×30 mL×1 min) and DCM (3×30 mL×1 min). A small sample of resin was removed, treated with 1:4 HFIPA/DCM, and the progress of the reaction was monitored by HPLC (HPLC Method 1). The chromatogram resulting from this HPLC analysis indicated that the coupling of phenylalanine was >90% complete, with the coupled peptide exhibiting a retention time of 25.1 minutes. The resin was treated with 5% piperidine in 1:1 NMP/DCM (30 mL) for 10 minutes followed by treatment with 20% piperidine in NMP (30 mL) for 15 minutes. The resin was sequentially washed with NMP (3×30 mL×1 min) and DCM (3×30 mL×1 min). The protected peptide was cleaved from the resin by treating the resin-supported peptide with 1:4 hexafluoroisopropanol/DCM (2×50 mL×10 min). The resin was washed with DCM (4×30 mL×5 min). The cleavage solutions and DCM washes were combined and the solvents removed in vacuo on a rotary evaporator. The resulting foam was dried under high vacuum overnight to yield 4.23 g of crude product as an orange foam. The crude linear protected hexapeptide product was analyzed by HPLC (HPLC Method 1). The chromatogram resulting from this analysis exhibited predominantly one peak with a retention time of 19.8 minutes.

Step 8. cyclo-{Tyr-D-Trp-Lys-Thr-Phe-(N—CH$_3$)Hcy}. Crude linear protected hexapeptide (4.23 g; 2.99 mmol, 2.75 mmol assumed) was dissolved in 100 mL of anhydrous DMF. DIEA (0.48 mL, 2.75 mmol) was added followed by the addition of HATU reagent (1.05 g, 2.75 mmol). An aliquot (15 μL) of the reaction mixture was removed and diluted with 150 μL of 0.1% (v/v) TFA in 9:1 (v/v) acetonitrile/water. The solution was analyzed by C18 reversed-phase analytical HPLC (HPLC Method 1). Stirring was continued at room temperature while following the progress of the reaction by HPLC. After 2 hours the cyclization was judged complete, with the disappearance of starting material (retention time=19.9 min) and the appearance of product (retention time=23.8 min). A solution of trifluoroacetic acid (TFA: 212 μL, 2.75 μmol) in H$_2$O (20 mL) was added and the solvents were removed by concentrating the reaction mixture on a rotary evaporator under high vacuum. The crude cyclic protected product was treated with DCM (30 mL) and the resulting suspension allowed to stand for 30 min. The solids were filtered off and washed with DCM (10 mL). The combined filtrates were treated with triisopropylsilane (1 mL), ethanedithiol (1 mL) and a solution of 1:20 H$_2$O/TFA (40 mL). After 1 hour the deprotection mixture was concentrated in vacuo and dissolved in 0.1% (v/v) TFA in 9:1 (v/v) acetonitrile/water (B buffer, 40 nL). This solution was diluted with 0.1% (v/v) TFA in H$_2$O (A buffer, 100 mL). The resulting suspension was filtered through a pad of diatomaceous earth which was subsequently washed with 20% B/A. The combined filtrate was split into four 40 ml portions and each portion was individually applied to a preparative HPLC column equilibrated in 15% B/A. The column was eluted with 15% to 28% B/A over 5 min and 28% to 33% B/A over 25 minutes. Fractions were collected and analyzed by HPLC method

| HPLC Method 2: | |
|---|---|
| Column: | Vydac C18, 4.6 mm × 250 mm |
| Solvent A: | 0.1% (v/v) TFA in water |
| Solvent B: | 0.1% (v/v) TFA in 9:1 (v/v) acetonitrile/water |
| Gradient: | 30%–35% B/A over 20 min, 100% B over 5 min |
| Flow Rate: | 1.2 mL/min |
| Injection Volume: | 50 μL |
| Detection: | UV (220 nm) |

Fractions containing product with a >95% purity by peak integration were combined and the acetonitrile was removed on a rotary evaporator. The resulting aqueous solution was frozen and lyophilized to yield cyclo-Tyr-D-Trp-Lys-Thr-Phe-(N—$CH_3$)Hcy as a white powder (510 mg). Analysis of the product by electrospray mass spectrometry (ESMS) confirmed the expected product. The expected exact molecular weight for cyclo-Tyr-D-Tri-Lys-Thr-Phe-(N—$CH_3$)Hcy($C_{44}H_{56}N_8O_8S_1$) was 856.4 daltons. The observed ESMS MH$^+$ peak was 857 daltons.

The structure of the novel pharmacophore is set forth below.

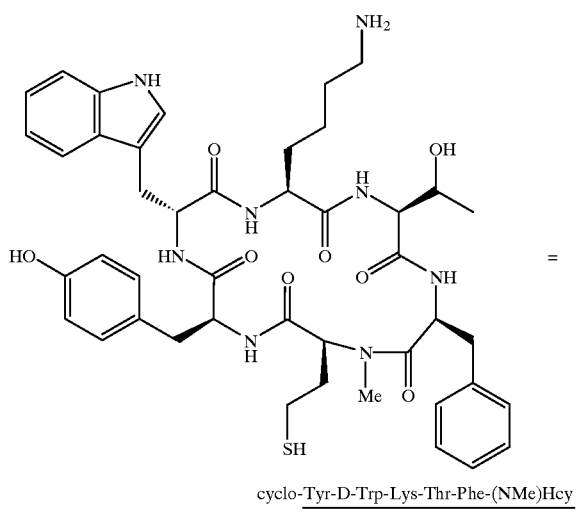

cyclo-Tyr-D-Trp-Lys-Thr-Phe-(NMe)Hcy

EXAMPLE 2

Synthesis of Chloroacetylated Peptidyl Chelator Precursor

The synthesis of a representative chloroacetylated peptidyl chelator precursor {$ClCH_2CO$-β-Dap(Boc)-Dab(Boc)-Cys(Trt)-Thr(tBu)(ol)} is described below.

Step 1. H-Cys(Trt)-Thr(tBu)(ol)-ClTrt. 2-Chlorotrityl resin-supported O-t-butyl-threoninol (4.6 g, 0.6 mmol/g, 2.76 mmol) was placed in peptide synthesis vessel and washed twice for 5 minutes with NMP (30 mL) with gentle agitation of the resin by argon gas. A small aliquot of resin was removed for ninhydrin analysis (as a control) and the resin washed with NMP (30 mL×1 min). In a separate flask, N-Fmoc-S-trityl cysteine (4.03 g, 6.88 mmol) and HATU reagent (2.56 g, 6.74 mmol) were dissolved in 30 mL of NMP. 2,4,6–Collidine (1.82 mL, 13.76 mmol) was added to the protected cysteine solution followed by immediate addition of the activated cysteine solution to the peptide synthesis vessel containing the resin-supported amino acid. The resin was agitated with a gentle stream of argon for 2.0 hrs. The solution was drained and the resin washed sequentially with NMP (3×30 mL×1 min) and DCM (3×30 mL×1 min). Ninhydrin analysis performed on a small portion of resin indicated that the reaction was complete. The resin was treated with 5% piperidine in 1:1 NMP/DCM (30 mL) for 10 minutes followed by treatment with 20% piperidine in NMP (30 mL) for 15 minutes. The resin was sequentially washed with NMP (3×30 mL×1 min) and DCM (3×30 mL×1 min). A small aliquot of resin was removed for ninhydrin analysis (as a control) and the resin washed with NMP (30 mL).

Step 2. H-Dab(Boc)-Cys(Trt)-Thr(tBu)(ol)-ClTrt. N-α-Fmoc-N-γ-Boc-2,4-(S)-diaminobutyric acid (3.03 g, 6.88 mmol) and HATU reagent (2.56 g, 6.74 mmol) were dissolved in 30 mL of NMP. DIEA (2.40 mL, 13.76 mmol) was added to the protected diaminobutyric acid solution. The flask was swirled for 1 minute and the contents added to the peptide synthesis vessel containing the resin-supported peptide from Step 1. The resin was agitated with a gentle stream of argon for 2.0 hrs. The solution was drained and the resin washed sequentially with NMP (3×30 mL×1 min) and DCM (3×30 mL×1 min). Ninhydrin analysis performed on a small portion of resin indicated that the reaction was complete. The resin was treated with 5% piperidine in 1:1 NMP/DCM (30 mL) for 10 minutes followed by treatment with 20% piperidine in NMP (30 mL) for 15 minutes. The resin was sequentially washed with NMP (3×30 mL×1 min) and DCM (3×30 mL×1 min). A small aliquot of resin was removed for ninhydrin analysis (as a control) and the resin washed with NMP (30 mL).

Step 3. H-β-Dap(Boc)-Dab(Boc)-Cys(Trt)-Thr(tBu)(ol)-ClTrt. N-α-Boc-N-β-Fmoc-2,3-(S)-diaminopropionic acid (2.93 g, 6.88 mmol) and HATU reagent (2.56 g, 6.74 mmol) were dissolved in 30 mL of NMP. DIEA (2.40 mL, 13.76 mmol) was added to the protected tyrosine solution. The flask was swirled for 1 minute and the contents added to the peptide synthesis vessel containing the resin-supported peptide from Step 2. The resin was agitated with a gentle stream of argon for 2.0 hrs. The solution was drained and the resin washed sequentially with NMP (3×30 mL×1 min) and DCM (3×30 mL×1 min). Ninhydrin analysis performed on a small portion of resin indicated that the reaction was complete. The resin-supported peptide was treated with 5% piperidine in 1:1 NMP/DCM (30 mL) for 10 minutes followed by treatment with 20% piperidine in NMP (30 mL) for 15 minutes. The resin was sequentially washed with NMP (3×30 mL×1 min) and DCM (3×30 mL×1 min). A small aliquot of resin was removed for ninhydrin analysis (as a control) and the resin washed with NMP (30 mL).

Step 4. $ClCH_2CO$-β-Dap(Boc)-Dab(Boc)-Cys(Trt)-Thr(tBu)(ol). Chloroacetic acid (0.65 mg, 6.88 mmol) was dissolved in 20 mL of NMP and a solution of 1:1 HBTU reagent/HOBt in DMF (0.45 M) (15.0 mL, 6.74 mmol) was added, followed by the addition of DIEA (2.40 mL, 13.76 mmol). The flask was swirled for 1 minute and the contents added to the peptide synthesis vessel containing the resin-supported amino acid from Step 3. The resin was agitated with a gentle stream of argon for 1.0 hrs. The solution was drained and the resin washed sequentially with NMP (3×30 mL×1 min) and DCM (3×30 mL×1 min). Ninhydrin analysis performed on a small portion of resin indicated that the reaction was complete. The resin-supported peptide was treated with 1% TFA (v/v) in DCM (60 mL, 7.79 mmol of TFA) for 15 minutes. The cleavage solution was filtered off and DIEA (2.7 mL, 15.6 mmol) was added to the cleavage solution. The resin was washed with DCM (3×60 mL×3 min) and the washes added to the solution of cleaved peptide. The volatiles were removed in vacuo on a rotary evaporator. The crude protected peptide was dissolved in 0.1% (v/v) TFA in 9:1 (v/v) acetonitrile/water (60 mL). The solution was divided into two equal fractions that were individually applied to a preparative HPLC column equilibrated in 0.1% (v/v) TFA in 1:1 (v/v) acetonitrile/water. The column was eluted with 50% to 100% B/A over 25 minutes and fractions containing product (retention time=16.4 min using HPLC method 1) with a purity of greater than 90% by peak integration were combined. A majority of the acetonitrile was removed on a rotary evaporator and the resulting aqueous suspension frozen and lyophilized to yield product as a white solid (970 mg). Analysis of the product by ESMS confirmed the expected product. The expected exact molecular weight for ClCH$_2$CO-β-Dap(Boc)-Dab(Boc)-Cys(Trt)-Thr(tBu)(ol) ($C_{49}H_{69}N_6O_{10}S_1Cl_1$) was 968.5 daltons. The observed ESMS MH$^+$ peak was 969 daltons.

EXAMPLE 3

Synthesis of Pharmacophore-Chelator Conjugate

The reaction between the somatostatin receptor-binding pharmacophore cyclo-Tyr-D-Trp-Ls-Thr-Phe-(N—CH$_3$)Hcy and the peptidyl chelator precursor ClCH$_2$CO-β-Dap(Boc)-Dab(Boc)-Cys(Trt)-Thr(tBu)(ol) to produce a pharmacophore-chelator conjugate of the invention is described below.

Step 1. cyclo-Tyr-D-Trp-Lys-Thr-Phe-(N—CH$_3$)Hcy(CH$_2$CO-β-Dap(Boc)-Dab(Boc)-Cys(Trt)-Thr-(tBu)(ol)). cyclo-Tyr-D-Trp-Lys-Thr-Phe-(N—CH$_3$)Hcy trifluoroacetate (30 mg, 30.9 μmol) and CH$_2$CO-β-Dap(Boc)-Dab(Boc)-Cys(Trt)-Thr(tBu)(ol) (36 mg, 37 μmol) were dissolved in DMF (3.0 mL) under an atmosphere of argon. To this solution was added a carbonate buffer solution (0.15 M, pH=10.0, 2.0 mL). The reaction mixture was stirred under an atmosphere of argon overnight. 0.1% (v/v) TFA in water (Buffer A, 20 mL) was added and the volatiles were removed in vacuo on a rotary evaporator to yield the crude protected conjugate as a solid.

Step 2. cyclo-Tyr-D-Trp-Lys-Thr-Phe-(N—CH$_3$)Hcy(CH$_2$CO-β-Dap-Dab-Cys-Thr(ol)). The crude protected conjugate produced in Step 1 was treated with a mixture of 55:40:2.5:1.5:1 TFA/DCM/water/triisopropylsilane/ethanedithiol (10 mL) for 1.5 hours. The deprotection mixture was diluted with cold ether (200 mL). This resulting precipitate was filtered off in a sintered glass funnel and washed with cold ether (2×20 mL) to yield crude product as an off-white solid. The crude product was dissolved in a 1:1 mixture of 0.1% (v/v) TFA in 9:1 (v/v) acetonitrile/water (B buffer)/A buffer (5 mL) and diluted with A buffer (20 mL). The resulting solution was applied to a preparative HPLC column which had been equilibrated in A buffer. The column was eluted with a gradient of 20% to 35% B/A over 25 minutes. The fractions were analyzed by HPLC using HPLC method 3.

| HPLC Method 3: | |
|---|---|
| Column: | Vydac C18, 4.6 mm × 250 mm |
| Solvent A: | 0.1% (v/v) TFA in water |
| Solvent B: | 0.1% (v/v) TFA in 9:1 (v/v) acetonitrile/water |
| Gradient: | 20%–50% B/A over 20 min, 100% B over 5 min |
| Flow Rate: | 1.2 mL/min |
| Injection Volume: | 50 μL |
| Detection: | UV (220 nm) |

Fractions containing pure product (retention time=10.0 min) with a purity of greater than 95% by peak integration were combined and the acetonitrile removed on a rotary evaporator. The resulting aqueous solution was frozen and lyophilized to yield a white powder (32 mg). Analysis of the product by ESMS confirmed the expected product. The expected exact molecular weight for cyclo-Tyr-D-Trp-Lys-Thr-Phe-(N—CH$_3$)Hcy(CH$_2$CO-β-Dap-Dab-Cys-Thr(ol))} ($C_{60}H_{86}N_{14}O_{14}S_2$) was 1290.6 daltons. The observed ESMS MH$^+$ peak was 1292 daltons.

TABLE 1

| Compound | MW (avg.) | ESMS M + H$^+$ |
|---|---|---|
| cyclo-YW$_D$KTF.(N—CH$_3$)Hcy(CH$_2$CO.β-Dap.YC.T(ol) | 1354.6 | 1355 |
| cyclo-YW$_D$KTF.(N—CH$_3$)Hcy(CH$_2$CO.β-Dap.F(4-NH$_2$).CT | 1367.6 | 1368 |
| cyclo-YW$_D$KTF.(N—CH$_3$)Hcy(CH$_2$CO.β-Dap.F(4-NH$_2$).CTS | 1454.6 | 1455 |
| cyclo-YW$_D$KTF.(N—CH$_3$)Hcy(CH$_2$CO.β-Dap.F(4-F).C.T(ol)) | 1356.6 | 1357 |
| cyclo-YW$_D$KTF.(N—CH$_3$)Hcy(CH$_2$CO.β-Dap.F(4-NH$_2$).C.T(ol)) | 1343.6 | 1354 |
| cyclo-YW$_D$KTF.(N—CH$_3$)Hcy(CH$_2$CO.β-Dap.HC.T(ol)) | 1328.5 | 1329 |
| cyclo-YW$_D$KTF.(N—CH$_3$)Hcy(CH$_2$CO.β-Dap.RC.T(ol)) | 1346.6 | 1348 |
| cyclo-YW$_D$KTF.(N—CH$_3$)Hcy(CH$_2$CO.β-Dap.GCK.amide) | 1288.5 | 1289 |
| cyclo-YW$_D$KTF.(N—CH$_3$)Hcy(CH$_2$CO.β-Dap.SC.T(ol)) | 1278.6 | 1279 |
| cyclo-YW$_D$KTF.(N—CH$_3$)Hcy(CH$_2$CO.β-Dap.Dab.C.T(ol)) | 1291.6 | 1292 |
| cyclo-YW$_D$KTF.(N—CH$_3$)Hcy(CH$_2$CO.β-Dap.Dab.C.S(ol)) | 1277.5 | 1278 |
| cyclo-YW$_D$KTF.(N—CH$_3$)Hcy(CH$_2$CO.SSC.NH(CH$_2$CH$_2$O)$_2$CH$_2$CH$_2$NH$_2$) | 1322.6 | 1323 |
| cyclo-YW$_D$KTF.(N—CH$_3$)Hcy(CH$_2$CO.GKC.amide) | 1202.5 | 1203 |
| cyclo-YW$_D$KTF.(N—CH$_3$)Hcy(CH$_2$CO.β-Dap.Orn.C.T(ol)) | 1305.6 | 1306 |
| cyclo-YW$_D$KTF.(N—CH$_3$)Hcy(CH$_2$CO.SKC.amide) | 1232.5 | 1233 |
| cyclo-YW$_D$KTF.(N—CH$_3$)Hcy(CH$_2$CO.β-Dap.KC.T(ol)) | 1319.6 | 1320 |
| cyclo-YW$_D$KTF.(N—CH$_3$)Hcy(CH$_2$CO.SSCK.amide) | 1319.6 | 1320 |
| cyclo-YW$_D$KTF.(N—CH$_3$)Hcy(CH$_2$CO.SSC.NHCH$_2$CH$_2$OCH$_2$CH$_2$NH$_2$) | 1278.5 | 1279 |
| cyclo-YW$_D$KTF.(N—CH$_3$)Hcy(CH$_2$CO.SSCR.amide) | 1346.6 | 1348 |
| cyclo-YW$_D$KTF.(N—CH$_3$)Hcy(CH$_2$CO.KGC.amide) | 1202.5 | 1203 |
| cyclo-YW$_D$KTF.(N—CH$_3$)Hcy(CH$_2$CO.β-Dap.KC.amide) | 1230.6 | 1231 |

TABLE 1-continued

| Compound | MW (avg.) | ESMS M + H⁺ |
|---|---|---|
| cyclo-YW<sub>D</sub>KTF.(N—CH<sub>3</sub>)Hcy(CH<sub>2</sub>CO.GGCR.amide) | 1286.6 | 1288 |
| cyclo-YW<sub>D</sub>KTF.(N—CH<sub>3</sub>)Hcy(CH<sub>2</sub>CO.β-Dap.GC.T(ol)) | 1248.6 | 1249 |
| cyclo-YW<sub>D</sub>KTF.(N—CH<sub>3</sub>)Hcy(CH<sub>2</sub>CO.S.Dab.C.S(ol)) | 1278.5 | 1279 |
| cyclo-YW<sub>D</sub>KTF.(N—CH<sub>3</sub>)Hcy(CH<sub>2</sub>CO.β-Dap.Dap.C.T(ol)) | 1277.5 | 1278 |
| cyclo-YW<sub>D</sub>KTF.(N—CH<sub>3</sub>)Hcy(CH<sub>2</sub>CO.S.Dap.C.amide) | 1190.5 | 1191 |
| cyclo-YW<sub>D</sub>KTF.(N—CH<sub>3</sub>)Hcy(CH<sub>2</sub>CO.SSC.Dap.amide) | 1277.5 | 1278 |
| cyclo-YW<sub>D</sub>KTF.(N—CH<sub>3</sub>)Hcy(CH<sub>2</sub>CO.SSCK.T(ol)) | 1407.7 | 1408 |
| cyclo-YW<sub>D</sub>KTF.(N—CH<sub>3</sub>)Hcy(CH<sub>2</sub>CO.TGGC.amide) | 1232.5 | 1255[1] |
| cyclo-(N—CH<sub>3</sub>)-FW<sub>D</sub>KTF(N—CH<sub>3</sub>)Hcy(CH<sub>2</sub>CO.β-Dap.KC.T(ol)) | 1318.6 | 1320 |
| cyclo-YW<sub>D</sub>KTF.(N—CH<sub>3</sub>)Hcy(CH<sub>2</sub>CO.δ-Orn.GC.amide)] | 1188.5 | 1211[1] |
| cyclo-YW<sub>D</sub>KTF.(N—CH<sub>3</sub>)Hcy(CH<sub>2</sub>CO.GGCH.amide) | 1268.5 | 1269 |
| cyclo-YW<sub>D</sub>KTF.(N—CH<sub>3</sub>)Hcy(CH<sub>2</sub>CO.GGC.F(4-NH<sub>2</sub>).amide) | 1293.5 | 1294 |
| cyclo-YW<sub>D</sub>KTF.(N—CH<sub>3</sub>)Hcy(CH<sub>2</sub>CO.β-Dap.Dap.CT.amide) | 1305.6 | 1306 |
| cyclo-YW<sub>D</sub>KTF.(N—CH<sub>3</sub>)Hcy(CH<sub>2</sub>CO.SSCT.NH(CH<sub>2</sub>CH<sub>2</sub>O)<sub>2</sub>CH<sub>2</sub>CH<sub>2</sub>NH<sub>2</sub>) | 1422.6 | 1423 |

[1](M + Na⁺)

EXAMPLE 4

Radiolabeling of Compounds of the Invention

A. Placebo Vial Method for Radiolabeling with $^{99m}$Tc

Approximately 100 μg of each compound as 100 μL of a 1 mg/mL TFA salt solution dissolved in 0.9% saline was added to a "placebo vial", containing lyophilized 5 mg sodium glucoheptonate dihydrate, 50 μg stannous chloride dihydrate, and 100 μg disodium edetate dihydrate. The vial was then reconstituted with sodium pertechnetate $^{99m}$Tc (15 to 25 mCi) and saline such that the total volume was 1.1 mL. Following reconstitution, the vials were incubated at 100° C. in a water bath for 10–12 minutes.

The purity of the $^{99m}$Tc-labeled compound was determined by reverse-phase analytical HPLC using the following conditions: a Zorbax 300SB C18, 4μ, 4.6 mm×250 mm analytical column was loaded with each radiolabeled compound, and the compound eluted at a solvent flow rate equal to .1.2 mL/min. Gradient elution was performed using a linear gradient of 20–50% Solvent B/Solvent A (Solvent A is 0.1% (v/v) trifluoroacetic acid (TFA) in water and Solvent B is 0.1% (v/v) TFA in 90/10 (v/v) acetonitrile/water) over 20 minutes; followed by a linear gradient of 50–100% Solvent B/Solvent A over four minutes and 100%, Solvent B/Solvent A for three minutes (Method 1).

Radioactive components were detected in the HPLC method using an in-line radiometric detector linked to a computerized data collection and analysis system (Waters Millenium). $^{99m}$Tc-glucoheptonate, $^{99m}$Tc-edetate, and $^{99m}$Tc-pertechnetate elute between one and four minutes under these conditions, whereas the $^{99m}$Tc-labeled compounds eluted after a much greater time. The radiochemical purity (as determined by the % area of the main $^{99m}$Tc product peaks) was ≧80%.

The purity of the $^{99m}$Tc-labeled compound was also determined by TLC quality control analysis. The radiolabeled peptide samples were spotted at the origin of each of two Gelman ITLC-SG strips. One strip each was developed in saturated saline (SAS) and 1:1 (v:v) methanol:1 M ammonium acetate (MAM) and allowed to dry. The SAS strips were cut at $R_f$ 0.75 and the MAM strip was cut at $R_f$ 0.40. The portions of the strips were counted for radioactivity in a dose calibrator, and the percent activity of the top and bottom portions of each strip calculated. The radiochemical purity of each sample was calculated as follows:

Purity by TLC=% bottom (SAS)–% bottom (MAM) The radiochemical purity by TLC was ≧90%.

TABLE 2

Radiochemical Purity Data--$^{99m}$Tc

| Compound | RCP HPLC | RCP TLC |
|---|---|---|
| cyclo-YW<sub>D</sub>KTF.(N—CH<sub>3</sub>)Hcy(CH<sub>2</sub>CO.β-Dap.YC.T(ol) | 87 | 98 |
| cyclo-YW<sub>D</sub>KTF.(N—CH<sub>3</sub>)Hcy(CH<sub>2</sub>CO.β-Dap.F(4-NH<sub>2</sub>).CT | 83 | 97 |
| cyclo-YW<sub>D</sub>KTF.(N—CH<sub>3</sub>)Hcy(CH<sub>2</sub>CO.β-Dap.F(4-NH<sub>2</sub>).CTS | 88 | 93 |
| cyclo-YW<sub>D</sub>KTF.(N—CH<sub>3</sub>)Hcy(CH<sub>2</sub>CO.β-Dap.F(4-F).C.T(ol)) | 86 | 99 |
| cyclo-YW<sub>D</sub>KTF.(N—CH<sub>3</sub>)Hcy(CH<sub>2</sub>CO.β-Dap.F(4-NH<sub>2</sub>).C.T(ol)) | 88 | 98 |
| cyclo-YW<sub>D</sub>KTF.(N—CH<sub>3</sub>)Hcy(CH<sub>2</sub>CO.β-Dap.HC.T(ol)) | 92 | 96 |
| cyclo-YW<sub>D</sub>KTF.(N—CH<sub>3</sub>)Hcy(CH<sub>2</sub>CO.β-Dap.RC.T(ol)) | 90 | 96 |
| cyclo-YW<sub>D</sub>KTF.(N—CH<sub>3</sub>)Hcy(CH<sub>2</sub>CO.β-Dap.GCK.amide) | 82 | 92 |
| cyclo-YW<sub>D</sub>KTF.(N—CH<sub>3</sub>)Hcy(CH<sub>2</sub>CO.β-Dap.SC.T(ol)) | 92 | 96 |
| cyclo-YW<sub>D</sub>KTF.(N—CH<sub>3</sub>)Hcy(CH<sub>2</sub>CO.β-Dap.Dab.C.T(ol)) | 90 | 94 |
| cyclo-YW<sub>D</sub>KTF.(N—CH<sub>3</sub>)Hcy(CH<sub>2</sub>CO.β-Dap.Dab.C.S(ol)) | 88 | 98 |
| cyclo-YW<sub>D</sub>KTF.(N—CH<sub>3</sub>)Hcy(CH<sub>2</sub>CO.SSC.NH(CH<sub>2</sub>CH<sub>21</sub>O)<sub>2</sub>CH<sub>2</sub>CH<sub>2</sub>NH<sub>2</sub>) | 83 | 95 |
| cyclo-YW<sub>D</sub>KTF.(N—CH<sub>3</sub>)Hcy(CH<sub>2</sub>CO.GKC.amide) | 93 | 97 |
| cyclo-YW<sub>D</sub>KTF.(N—CH<sub>3</sub>)Hcy(CH<sub>2</sub>CO.β-Dap.Orn.C.T(ol)) | 96 | 97 |
| cyclo-YW<sub>D</sub>KTF.(N—CH<sub>3</sub>)Hcy(CH<sub>2</sub>CO.SKC.amide | — | 92 |
| cyclo-YW<sub>D</sub>KTF.(N—CH<sub>3</sub>)Hcy(CH<sub>2</sub>CO.β-Dap.KC.T(ol)) | 82 | 97 |
| cyclo-YW<sub>D</sub>KTF.(N—CH<sub>3</sub>)Hcy(CH<sub>2</sub>CO.SSCK.amide) | 94 | 98 |
| cyclo-YW<sub>D</sub>KTF.(N—CH<sub>3</sub>)Hcy(CH<sub>2</sub>CO.SSC.NHCH<sub>2</sub>CH<sub>2</sub>OCH<sub>2</sub>CH<sub>2</sub>NH<sub>2</sub>) | 76[1] | 92 |
| cyclo-YW<sub>D</sub>KTF.(N—CH<sub>3</sub>)Hcy(CH<sub>2</sub>CO.SSCR.amide) | 87 | 95 |
| cyclo-YW<sub>D</sub>KTF.(N—CH<sub>3</sub>)Hcy(CH<sub>2</sub>CO.KGC.amide) | 87 | 98 |

TABLE 2-continued

Radiochemical Purity Data--$^{99m}$Tc

| Compound | RCP HPLC | RCP TLC |
|---|---|---|
| cyclo-YW$_D$KTF.(N—CH$_3$)Hcy(CH$_2$CO.β-Dap.KC.amide) | 88 | 96 |
| cyclo-YW$_D$KTF.(N—CH$_3$)Hcy(CH$_2$CO.GGCR.amide) | 88 | 97 |
| cyclo-YW$_D$KTF.(N—CH$_3$)Hcy(CH$_2$CO.β-Dap.GC.T(ol)) | 92 | 95 |
| cyclo-YW$_D$KTF.(N—CH$_3$)Hcy(CH$_2$CO.S.Dab.C.S(ol)) | — | 96 |
| cyclo-YW$_D$KTF.(N—CH$_3$)Hcy(CH$_2$CO.β-Dap.Dap.C.T(ol)) | — | 98 |
| cyclo-YW$_D$KTF.(N—CH$_3$)Hcy(CH$_2$CO.S.Dap.C.amide) | — | 96 |
| cyclo-YW$_D$KTF.(N—CH$_3$)Hcy(CH$_2$CO.SSC.Dap.amide) | — | 92 |
| cyclo-YW$_D$KTF.(N—CH$_3$)Hcy(CH$_2$CO.SSCK.T(ol)) | 91 | 95 |
| cyclo-YW$_D$KTF.(N—CH$_3$)Hcy(CH$_2$CO.TGGC.amide) | 95 | 96 |
| cyclo-(N—CH$_3$)-FW$_D$KTF(N—CH$_3$)Hcy(CH$_2$CO.β-Dap.KC.T(ol)) | 90 | 95 |
| cyclo-YW$_D$KTF.(N—CH$_3$)Hcy(CH$_2$CO.δ-Orn.GC.amide)] | 75 | 90 |
| cyclo-YW$_D$KTF.(N—CH$_3$)Hcy(CH$_2$CO.GGCH.amide) | 88 | 99 |
| cyclo-YW$_D$KTF.(N—CH$_3$)Hcy(CH$_2$CO.GGC.F(4-NH$_2$).amide) | 82[2] | 92 |

B. Method for Radiolabeling with $^{188}$Re

A compound of the invention having the structure set forth below was radiolabeled with $^{188}$Re using the following procedure.

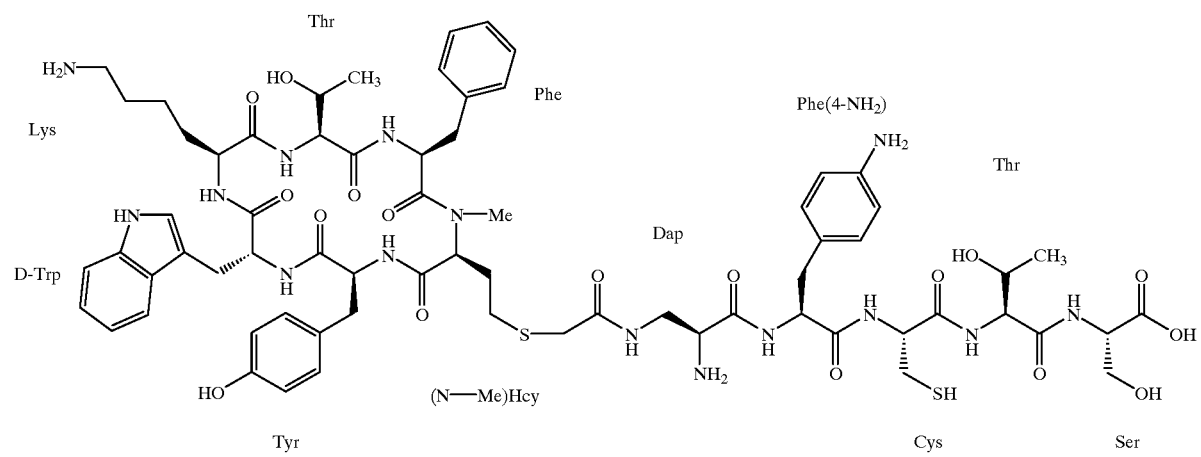

In the specification and the claims, this compound is represented as cyclo-Tyr-D-Trp-Lys-Thr-Phe-(N—CH$_3$)Hcy(CH$_2$CO-β-Dap-Phe(4—NH$_2$)-Cys-Thr-Ser) and in the tables of the examples the compound is represented as cyclo-YW$_D$KTF.(N—CH$_3$)Hcy(CH$_2$CO.β-Dap.F(4-NH$_2$).CTS).

Shielding adequate for protection against β-radiation, γ-radiation, and x-ray exposure must be positioned between the reaction vessels and the person performing the labeling. The trifluoroacetate salt of the peptide (70 μg) was formulated with 25 mg Sodium α-D-Glucoheptonate Dihydrate, 850 μg Tin (II) Chloride Dihydrate ACS,100 μg Edetate Disodium USP, and Water for Injection USP q.s. to 1.0 mL, adjusted to pH 7.4±0.1 with sodium hydroxide and/or hydrochloric acid and lyophilized. The lyophilized formulation was reconstituted with 1 mL $^{188}$Re eluate from a $^{188}$W/$^{188}$Re-generator in 0.9% Sodium Chloride Injection USP. The reconstituted formulation was incubated for 15 minutes in a boiling water bath. Four mL of a saline solution containing 20 mg gentisic acid (as the sodium salt, monohydrate) and 10 mg ascorbic acid was added and the solution allowed to cool for 15 minutes at room temperature. The cooled solution was filtered though a 0.22 micron filter into a sterile, preferably evacuated, nitrogen-filled vial.

The $^{188}$Re-labeled peptide is stable (≧90% radiochemical purity by TLC and ≧85% radiochemical purity by HPLC) for at least 3 hours after preparation, when stored at room temperature.

EXAMPLE 5

SSTR Affinities of Compounds of the Invention

[$^{125}$I-Tyr$^{11}$] somatostatin-14 ([$^{125}$I]SST-14) was obtained from Amersham. Unlabeled somatostatin-14 was purchased either from BACHEM (Torrance, Calif.) or from Sigma Chemical Co. (St. Louis, Mo.). Protease inhibitors, leupeptin, aprotinin, bacitracin, and benzamidine and other reagents were obtained from Sigma. Protease inhibitors were prepared in dimethylsulfoxide (DMSO) at a concentration 500×higher than the final assay concentration. The prepared protease solution was stored at −20° C. and diluted with the buffer solution before use.

Membrane preparations used in these studies were prepared from two commercially available tumor cell lines, the human small cell lung cancer cell line, NCI-H69, and the rat pancreatic tumor cell line, AR42J, obtained from American Type Culture Collection (ATCC) (Manassas, Va.). NCI-H69 cells were maintained by serial passage in RPMI 1640 with 10% fetal calf serum. AR42J cells were maintained in F-12K medium containing 20% fetal calf serum. Cells in culture flasks were incubated at 37° C. with 5% $CO_2$ in air atmosphere following the recommendations of the "Product Sheet" from ATCC.

Cultured cells were first detached from plates with phosphate-buffered saline, pH 7.4, containing 2 mM EDTA, and centrifuged at 1,500×g for 10 min. Cells were then resuspended in 5–10 mL of the homogenization buffer (1 mM sodium bicarbonate, pH 7.4, 1 mM EDTA, 1 mM EGTA, 2.5 mM DTT, 5 μg/mL leupeptin, 5 μg/mL aprotinin, 100 μg/mL bacitracin, 100 μg/mL benzamidine) for 10 min on ice. The cells were lysed for 30 sec twice in a polytron with a setting at 5. The lysate was centrifuged at 1,000×g for 10 min at 4° C. The supernatant was centrifuged at 40,000×g for 20 min at 4° C. This step was repeated twice with the homogenization buffer in the absence of protease inhibitors. The pellet was then resuspended at 1–5 mg membrane protein/mL in 25 mM Tris, pH 7.4 without the addition of protease inhibitors and the membranes were stored at −80° C. before use. Membrane protein concentration was determined spectroscopically using the bicinchonic acid (BCA) protein assay kit (Pierce Chemical Inc. (Rockford, Ill.).

All [$^{125}$I]SST-14 binding assays were performed in 0.5 mL binding buffer containing 50 mM HEPES, pH 7.5, 10 mM $MgCl_2$, 0.25% BSA (w/v) containing protease inhibitors (same as above) and incubated at 37° C. for 45 minutes. After incubation, samples were kept at 4° C. and rapidly filtered under vacuum through a Whatman GF/B glass fiber filter with a 12-well harvester (Skatron Instruments Inc., Sterling, Va.). The filter was washed for 9 seconds with cold 50 mM HEPES, pH 7.5, 10 mM $MgCl_2$, 0.25% BSA (w/v). Thirty-five pmole of [$^{125}$I]SST-14 from Amersham was used in each tube. Peptides were solubilized in DMSO and serially diluted with DMSO. Five μL of peptide in DMSO was used to obtain the final concentration. DMSO (5 μL) was added to the tube without the addition of any peptide or unlabeled SST-14, so that each tube contained 1% DMSO. Non-specific binding was defined as the binding of [$^{125}$I] SST-14 which was not displaceable with an excess of unlabeled SST-14 at a concentration of $1×10^{-6}$ M. The bound [$^{125}$I]SST-14 without or with excess unlabeled SST-14 ($1×10^{-6}$ M) was defined as total binding and nonspecific binding, respectively. The difference between total and non-specific binding was defined as specific binding. The percent inhibition (% Inh) by peptide was expressed as % Inh=(total binding−total binding in the presence of peptide)/ specific binding×100%

Inclusion of protease inhibitors in homogenizing medium as well as assay buffer is essential to maintain the integrity of both [$^{125}$I]SST-14 and somatostatin analogs for the receptor binding assay and to obtain optimal specific binding. The highest specific binding was observed when $MgCl_2$ (10 mM) was included. Membranes were finally resuspended in a sodium-free medium and receptor binding assays were performed in the absence of sodium ions.

The potency of the compounds of the invention in inhibiting the binding of [$^{125}$I]SST-14 to isolated membranes was expressed as the $IC_{50}$, defined as the concentration of compound inhibiting by 50% the specific binding. Binding isotherms indicated that many compounds bound to two classes of receptors. $IC_{50}$ values were calculated from the data by a computerized nonlinear, least squares curve-fitting program assuming two classes of receptor binding sites (GraphPad Prism, GraphPad Software, Inc., San Diego, Calif.).

TABLE 3

$IC_{50}$ Values for Uncomplexed Compounds

| Compound | NCI-H69 | |
|---|---|---|
| cyclo-YW$_D$KTF.(N—CH$_3$).Hcy. | $2.10 × 10^{-10}$ | |
| cyclo-YW$_D$KVF.(N—CH$_3$).Hcy. | $2.10 × 10^{-10}$ | |
| cyclo-YW$_D$KTF.(N—CH$_3$).Hcy(CH$_2$CO.TGGC.amide) | $1.63 × 10^{-9}$ | $2.43 × 10^{-5}$ |
| cyclo-YW$_D$KTF.(N—CH$_3$).Hcy(CH$_2$CO.δ-O.GC.amide) | $2.92 × 10^{-9}$ | |
| cyclo-YW$_D$KTF.(N—CH$_3$)Hcy(CH$_2$CO.β-Dap.KC.T(ol) | $3.46 × 10^{-10}$ | $2.34 × 10^{-7}$ |
| cyclo-YW$_D$KTF.(N—CH$_3$)Hcy(CH$_2$CO.SSC.NH(CH$_2$CH$_2$O)$_2$CH$_2$CH$_2$NH$_2$) | $6.45 × 10^{-10}$ | >$10^{-6}$ |
| cyclo-YW$_D$KTF.(N—CH$_3$)Hcy(CH$_2$CO.β-Dap.Dap.C.T(ol) | $4.49 × 10^{-10}$ | $4.68 × 10^{-8}$ |
| cyclo-YW$_D$KTF.(N—CH$_3$)Hcy(CH$_2$CO.β-Dap.Dab.C.T(ol) | $6.42 × 10^{-10}$ | >$10^{-6}$ |
| cyclo-YW$_D$KTF.(N—CH$_3$)Hcy(CH$_2$CO.β-Dap.O.C.T(ol) | $5.05 × 10^{-10}$ | $7.44 × 10^{-7}$ |
| cyclo-YW$_D$KTF.(N—CH$_3$)Hcy(CH$_2$CO.β-Dap.RC.T(ol) | $4.13 × 10^{-10}$ | <$10^{-12}$ |
| cyclo-YW$_D$KTF.(N—CH$_3$)Hcy(CH$_2$CO.β-Dap.F(4-NH$_2$).C.T(ol))] | $5.01 × 10^{-10}$ | <$10^{-12}$ |
| cyclo-YW$_D$KTF.(N—CH$_3$)Hcy(CH$_2$CO.β-Dap.S.C.T(ol) | $1.57 × 10^{-9}$ | <$10^{-12}$ |
| cyclo-YW$_D$KTF.(N—CH$_3$)Hcy(CH$_2$CO.β-Dap.HC.T(ol) | $8.61 × 10^{-10}$ | |
| cyclo-YW$_D$KTF.(N—CH$_3$)Hcy(CH$_2$CO.β-DapDab.C.S(ol) | $1.08 × 10^{-9}$ | |
| cyclo-YW$_D$KTF.(N—CH$_3$)Hcy(CH$_2$CO.S.Dab.C.S(ol) | | |
| cyclo-YW$_D$KTF.(N—CH$_3$)Hcy(CH$_2$CO.β-Dap.Dab.CT) | $1.25 × 10^{-9}$ | $1.25 × 10^{-9}$ |
| cyclo-YW$_D$KTF.(N—CH$_3$)Hcy(CH$_2$CO.β-Dap.F(4-NH$_2$).CT) | $6.41 × 10^{-10}$ | $6.41 × 10^{-10}$ |
| cyclo-YW$_D$KTF.(N—CH$_3$)Hcy(CH$_2$CO.β-Dap.F(4-NH$_2$).CTS) | $2.01 × 10^{-10}$ | $8.91 × 10^{-9}$ |
| cyclo-YW$_D$KTF.(N—CH$_3$)Hcy(CH$_2$CO.β-Dap.F(4-NH$_2$).CT.S(ol)) | $3.88 × 10^{-10}$ | $3.88 × 10^{-10}$ |

TABLE 4

IC$_{50}$ Values for Rhenium-Complexed Compounds

| Compound | NCI-H69 | |
|---|---|---|
| cyclo-YW$_D$KTF.(N—CH$_3$).Hcy(CH$_2$CO.δ-O.GC.amide) (ReO) | 3.83 × 10$^{-9}$ | 1.62 × 10$^{-6}$ |
| cyclo-YW$_D$KTF.(N—CH$_3$).Hcy(CH$_2$CO.TGGC.amide)(ReO) | 3.71 × 10$^{-9}$ | >10$^{-5}$ |
| cyclo-YW$_D$KTF.(N—CH$_3$).Hcy(CH$_2$CO.TGGC.amide)(ReO) | 3.88 × 10$^{-9}$ | >10$^{-5}$ |
| cyclo-YW$_D$KTF.(N—CH$_3$).Hcy(CH$_2$CO.GGCH.amide)(ReO) | 8.16 × 10$^{-9}$ | >10$^{-3}$ |
| cyclo-YW$_D$KTF.(N—CH$_3$).Hcy(CH$_2$CO.SSCK.amide)(ReO) | 1.55 × 10$^{-9}$ | >10$^{-3}$ |
| cyclo-YW$_D$KTF.(N—CH$_3$).Hcy(CH$_2$CO.KGC.amide)(ReO, α-N) | 5.00 × 10$^{-10}$ | 1.91 × 10$^{-7}$ |
| cyclo-YW$_D$KTF.(N—CH$_3$).Hcy(CH$_2$CO.KGC.amide)(ReO, ε-N) | 5.09 × 10$^{-10}$ | 2.47 × 10$^{-7}$ |
| cyclo-YW$_D$KTF.(N—CH$_3$).Hcy(CH$_2$CO.β-Dap.GCK.amide)(ReO, r.t. 12.3) | 4.30 × 10$^{-10}$ | 5.07 × 10$^{-6}$ |
| cyclo-YW$_D$KTF.(N—CH$_3$).Hcy(CH$_2$CO.β-Dap.GCK.amide)(ReO, r.t. 12.8), | 3.31 × 10$^{-10}$ | >10$^{-6}$ |
| cyclo-YW$_D$KTF.(N—CH$_3$).Hcy(CH$_2$CO.β-Dap.KC.T(ol)(ReO), | 6.47 × 10$^{-10}$ | >10$^{-6}$ |
| cyclo-YW$_D$KTF.(N—CH$_3$).Hcy(CH$_2$CO.SSCK.T(ol)(ReO) | 7.41 × 10$^{-10}$ | >10$^{-6}$ |
| cyclo-YW$_D$KTF.(N—CH$_3$).Hcy(CH$_2$CO.GKC.amide)(ReO) | 1.15 × 10$^{-10}$ | 1.88 × 10$^{-8}$ |
| cyclo-YW$_D$KTF.(N—CH$_3$).Hcy(CH$_2$CO.β-Dap.KC.amide)](ReO) | 4.99 × 10$^{-10}$ | 1.58 × 10$^{-11}$ |
| cyclo-YW$_D$KTF.(N—CH$_3$).Hcy(CH$_2$CO.SSCR.amide)(ReO) | 9.15 × 10$^{-10}$ | >10$^{-6}$ |
| cyclo-YW$_D$KTF.(N—CH$_3$).Hcy(CH$_2$CO.GGCR.amide)(ReO) | 6.18 × 10$^{-9}$ | 1.18 × 10$^{-10}$ |
| cyclo-YW$_D$KTF.(N—CH$_3$).Hcy(CH$_2$CO.GGCK.amide)(ReO) | 1.43 × 10$^{-9}$ | >10$^{-6}$ |
| cyclo-YW$_D$KTF.(N—CH$_3$).Hcy(CH$_2$CO.β-Dap.KC.amide)(ReO) | 8.90 × 10$^{-9}$ | 3.18 × 10$^{-10}$ |
| cyclo-YW$_D$KTF.(N—CH$_3$).Hcy(CH$_2$CO.β-Dap.KC.amide)(ReO) | 8.23 × 10$^{-9}$ | <10$^{-10}$ |
| cyclo-YW$_D$KTF.(N—CH$_3$).Hcy(CH$_2$CO.GGC.F(4-NH$_2$))(ReO) | 2.73 × 10$^{-10}$ | 2.73 × 10$^{-11}$ |
| cyclo-YW$_D$KTF.(N—CH$_3$).Hcy(CH$_2$CO.SKC.amide)(ReO) | 2.70 × 10$^{-10}$ | 1.26 × 10$^{-8}$ |
| cyclo-YW$_D$KTF.(N—CH$_3$).Hcy(CH$_2$CO.SSC.Dap.amide)(ReO) | 6.91 × 10$^{-10}$ | 9.76 × 10$^{-9}$ |
| cyclo-YW$_D$KTF.(N—CH$_3$).Hcy(CH$_2$CO.S.Dap.C.amide)(ReO) | 3.12 × 10$^{-10}$ | 1.56 × 10$^{-9}$ |
| cyclo-YW$_D$KTF.(N—CH$_3$).Hcy(CH$_2$CO.β-Dap.Dap.C.T(ol)(ReO) | 3.51 × 10$^{-10}$ | 5.36 × 10$^{-8}$ |
| cyclo-YW$_D$KTF.(N—CH$_3$).Hcy(CH$_2$CO.β-Dap.Dab.C.T(ol)(ReO) | 6.07 × 10$^{-10}$ | 1.37 × 10$^{-12}$ |
| cyclo-YW$_D$KTF.(N—CH$_3$).Hcy(CH$_2$CO.SSC.NH(CH$_2$CH$_2$O)$_2$CH$_2$CH$_2$NH$_2$)(ReO) | 4.89 × 10$^{-10}$ | 2.17 × 10$^{-12}$ |
| cyclo-YW$_D$KTF.(N—CH$_3$).Hcy(CH$_2$CO.β-Dap.O.C.T(ol)(ReO) | 4.75 × 10$^{-10}$ | 1.41 × 10$^{-12}$ |
| cyclo-YW$_D$KTF.(N—CH$_3$).Hcy(CH$_2$CO.β-DapDab.C.T(ol)(ReO) | 1.43 × 10$^{-10}$ | 1.02 × 10$^{-7}$ |
| cyclo-YW$_D$KTF.(N—CH$_3$).Hcy(CH$_2$CO.β-Dap.F(4-NH$_2$).C.T(ol))(ReO). | 1.22 × 10$^{-10}$ | 4.30 × 10$^{-7}$ |
| cyclo-YW$_D$KTF.(N—CH$_3$).Hcy(CH$_2$CO.β-Dap.S.C.T(ol)(ReO). | 5.13 × 10$^{-10}$ | 2.63 × 10$^{-12}$ |
| cyclo-YW$_D$KTF.(N—CH$_3$).Hcy(CH$_2$CO.β-Dap.HC.T(ol)ReO. | 2.23 × 10$^{-10}$ | 6.03 × 10$^{-8}$ |
| cyclo-YW$_D$KTF.(N—CH$_3$).Hcy(CH$_2$CO.β-Dap.GC.T(ol)ReO | 2.22 × 10$^{-10}$ | 3.29 × 10$^{-9}$ |
| cyclo-YW$_D$KTF.(N—CH$_3$).Hcy(CH$_2$CO.β-DapDab.C.S(ol)ReO | 2.00 × 10$^{-10}$ | 2.67 × 10$^{-8}$ |
| cyclo-YW$_D$KTF.(N—CH$_3$).Hcy(CH$_2$CO.S.Dab.C.S(ol)ReO | 1.55 × 10$^{-9}$ | 1.14 × 10$^{-11}$ |
| cyclo-YW$_D$KTF.(N—CH$_3$).Hcy(CH$_2$CO.β-Dap.F(4-NH$_2$).CT.S(ol))ReO | 6.02 × 10$^{-10}$ | 4.13 × 10$^{-12}$ |
| cyclo-YW$_D$KTF.(N—CH$_3$).Hcy(CH$_2$CO.β-Dap.F(4-NH$_2$).CTS)ReO | 2.27 × 10$^{-10}$ | 1.47 × 10$^{-8}$ |
| cyclo-YW$_D$KTF.(N—CH$_3$).Hcy(CH$_2$CO.β-Dap.Dab.CT)ReO | 7.75 × 10$^{-10}$ | |
| cyclo-YW$_D$KTF.(N—CH$_3$).Hcy(CH$_2$CO.β-Dap.F(4-NH$_2$).CT)ReO | 4.45 × 10$^{-10}$ | |

TABLE 5

IC$_{50}$ Values for AR42J Cell Membranes

| Compound | | |
|---|---|---|
| cyclo-YW$_D$KTF.(N—CH$_3$)Hcy(CH$_2$CO.β-Dap.F(4-NH$_2$).CTS) | 4.33 × 10$^{-10}$ | 1.26 × 10$^{-12}$ |
| cyclo-YW$_D$KTF.(N—CH$_3$).Hcy(CH$_2$CO.β-Dap.Dab.C.T(ol)(ReO | 1.81 × 10$^{-10}$ | 5.08 × 10$^{-7}$ |
| cyclo-YW$_D$KTF.(N—CH$_3$).Hcy(CH$_2$CO.SSC.NH(CH$_2$CH$_2$O)$_2$CH$_2$CH$_2$NH$_2$)(ReO) | 2.17 × 10$^{-10}$ | 6.17 × 10$^{-3}$ |
| cyclo-YW$_D$KTF.(N—CH$_3$).Hcy(CH$_2$CO.SSC.NH(CH$_2$CH$_2$O)$_2$CH$_2$CH$_2$NH$_2$)(ReO) | 1.67 × 10$^{-10}$ | 8.99 × 10$^{-7}$ |
| cyclo-YW$_D$KTF.(N—CH$_3$).Hcy(CH$_2$CO.β-Dap.F(4-NH$_2$).C.T(ol))(ReO). | 9.00 × 10$^{-11}$ | >10$^{-6}$ |
| cyclo-YW$_D$KTF.(N—CH$_3$).Hcy(CH$_2$CO.β-Dap.F(4-NH$_2$).CTS)ReO | 4.96 × 10$^{-10}$ | 3.74 × 10$^{-12}$ |

EXAMPLE 6

Biodistributions of Compounds of the Invention

Rat pancreatic AR42J cells (ATCC, Rockville, Md., USA) were grown in Modified Ham's F12K medium (Cat. No. N-3520, Sigma, St. Louis, Mo., USA) containing 20% fetal bovine serum (FCS) (Cat. No. 1224, Lot No. 9702058, Sigma, St. Louis, Mo., USA) under sterile conditions in 95% humidity and 5% CO$_2$. At a density of approximately 10×10$^6$ cells per T150 flask, the cells were harvested with trypsin and collected by centrifugation at 2400 rpm (800×g) for 15 minutes in a benchtop centrifuge (IEC Centra-8 tabletop centrifuge, International Equipment Company, Needham, Mass., USA). The cells were resuspended in medium containing 20% FCS for implantation.

Six female nude mice (CrlLNU/NU-nuBR, 6–8 weeks old) were injected subcutaneously into the right flank with tumor cells (2×10$^7$/100 μL) in 20% matrigel (Collaborative Biomedical Products, Chicago, Ill., USA). Fourteen days after inoculation tumors were visible in all animals. Three weeks after inoculation, tumors were aseptically dissected, minced and implanted into 60 nude mice using a trochar. The tumor xenografts from the second passage were used for biodistribution studies.

A dose of approximately 50–100 μCi $^{99m}$Tc-labeled compound/mouse was injected intravenously in a total volume of 100 μL. Mice were sacrificed 90 minutes post-injection by decapitation and the trunk blood was collected. Tumors (1 to 3 per mouse), liver, gastrointestinal tract, kidneys, and samples of muscle from both legs (quadriceps femoralis) were collected, weighed, and counted for radioactivity. Biodistribution data for a number of $^{99m}$Tc-labeled compounds of the invention are presented in Table 6.

TABLE 6

Biodistribution Data--$^{99m}$Tc

| Compound | TUMOR % 1 dI/g | Kidneys % id/g | Spleen % ID | GI % ID | Urine % ID | T:M | T:B |
|---|---|---|---|---|---|---|---|
| cyclo-YW$_D$KTF.(N—CH$_3$)Hcy(CH$_2$CO.β-Dap.YC.T(ol) | 27.6 | 7.7 | 0.1 | 22 | 32 | 165 | 63 |
| cyclo-YW$_D$KTF.(N—CH$_3$)Hcy(CH$_2$CO.β-Dap.F(4-NH$_2$).CT | 25 | 5.7 | 0.08 | 14 | 53 | 129 | 59 |
| cyclo-YW$_D$KTF.(N—CH$_3$)Hcy(CH$_2$CO.β-Dap.F(4-NH$_2$).CTS | 24.7 | 4.8 | 0.21 | 8 | 59 | 127 | 29 |
| cyclo-YW$_D$KTF.(N—CH$_3$)Hcy(CH$_2$CO.β-Dap.F(4-F).C.T(ol)) | 23.5 | 4.7 | 0.17 | 24 | 20 | 124 | 25 |
| cyclo-YW$_D$KTF.(N—CH$_3$)Hcy(CH$_2$CO.β-Dap.F(4-NH$_2$).C.T(ol) | 31.8 | 6.5 | 0.08 | 11 | 48 | 188 | 81 |
| cyclo-YW$_D$KTF.(N—CH$_3$)Hcy(CH$_2$CO.β-Dap.HC.T(ol)) | 15.5 | 8.1 | 0.3 | 9 | 53 | 96 | 29 |
| cyclo-YW$_D$KTF.(N—CH$_3$)Hcy(CH$_2$CO.β-Dap.RC.T(ol)) | 15.2 | 17.6 | 0.1 | 4.8 | 58 | 94 | 34 |
| cyclo-YW$_D$KTF.(N—CH$_3$)Hcy(CH$_2$CO.β-Dap.GCK.amide) | 13.36 | 80.1 | 0.05 | 4 | 40 | 108 | 27 |
| cyclo-YW$_D$KTF.(N—CH$_3$)Hcy(CH$_2$CO.β-Dap.SC.T(ol)) | 12.6 | 6.1 | 0.06 | 8 | 59 | 144 | 31 |
| cyclo-YW$_D$KTF.(N—CH$_3$)Hcy(CH$_2$CO.β-Dap.Dab.C.T(ol)) | 11.7 | 6.6 | 0.08 | 3 | 84 | 43 | 13 |
| cyclo-YW$_D$KTF.(N—CH$_3$)Hcy(CH$_2$CO.β-Dap.Dab.C.S(ol)) | 10.8 | 13.9 | 0.04 | 2 | 73 | 89 | 30 |
| cyclo-YW$_D$KTF.(N—CH$_3$)Hcy(CH$_2$CO.SSC.NH(CH$_2$CH$_2$O)$_2$CH$_2$CH$_2$NH$_2$) | 10.6 | 17.8 | 0.05 | 3 | 70 | 132 | 44 |
| cyclo-YW$_D$KTF.(N—CH$_3$)Hcy(CH$_2$CO.GKC.amide) | 10.3 | 28.3 | 0.09 | 15 | 46 | 49 | 13 |
| cyclo-YW$_D$KTF.(N—CH$_3$)Hcy(CH$_2$CO.β-Dap.OC.T(ol)) | 10.3 | 28.8 | 0.05 | 2 | 73 | 96 | 24 |
| cyclo-YW$_D$KTF.(N—CH$_3$)Hcy(CH$_2$CO.SKC.amide) | 10.3 | 41.9 | 0.07 | 5 | 68 | 49 | 15 |
| cyclo-YW$_D$KTF.(N—CH$_3$)Hcy(CH$_2$CO.β-Dap.KC.T(ol)) | 10.2 | 26.8 | 0.04 | 3 | 65 | 104 | 48 |
| cyclo-YW$_D$KTF.(N—CH$_3$)Hcy(CH$_2$CO.SSCK.amide) | 9.2 | 25.1 | 0.04 | 6 | 72 | 71 | 26 |
| cyclo-YW$_D$KTF.(N—CH$_3$)Hcy(CH$_2$CO.SSC.NHCH$_2$CH$_2$OCH$_2$CH$_2$NH$_2$) | 9.1 | 54 | 0.07 | 5 | 68 | 70 | 19 |
| cyclo-YW$_D$KTF.(N—CH$_3$)Hcy(CH$_2$CO.SSCR.amide) | 8.6 | 31.6 | 0.05 | 6 | 37 | 50 | 11 |
| cyclo-YW$_D$KTF.(N—CH$_3$)Hcy(CH$_2$CO.KGC.amide) | 7.94 | 58.8 | 0.04 | 7 | 48 | 49 | 15 |
| cyclo-YW$_D$KTF.(N—CH$_3$)Hcy(CH$_2$CO.β-Dap.KC.amide) | 7.52 | 42.5 | 0.05 | 3 | 36 | 32 | 16 |
| cyclo-YW$_D$KTF.(N—CH$_3$)Hcy(CH$_2$CO.GGCR.amide) | 7.24 | 32.3 | 0.09 | 8 | 39 | 18 | 5 |
| cyclo-YW$_D$KTF.(N—CH$_3$)Hcy(CH$_2$CO.β-Dap.GC.T(ol)) | 7.1 | 4.5 | 0.07 | 19 | 43 | 56 | 13 |
| cyclo-YW$_D$KTF.(N—CH$_3$)Hcy(CH$_2$CO.S.Dab.C.S(ol)) | 7 | 21.1 | 0.04 | 3 | 76 | 65 | 18 |
| cyclo-YW$_D$KTF.(N—CH$_3$)Hcy(CH$_2$CO.β-Dap.Dap.C.T(ol)) | 6.4 | 7.9 | 0.04 | 7 | 85 | 64 | 16 |
| cyclo-YW$_D$KTF.(N—CH$_3$)Hcy(CH$_2$CO.S.Dap.C.amide) | 4.8 | 9.3 | 0.07 | 25 | 45 | 25 | 9 |
| cyclo-YW$_D$KTF.(N—CH$_3$)Hcy(CH$_2$CO.SSC.Dap.amide) | 4.5 | 12.6 | 0.07 | 8 | 65 | 23 | 8 |
| cyclo-YW$_D$KTF.(N—CH$_3$)Hcy(CH$_2$CO.SSCK.T(ol)) | 4.3 | 13.6 | 0.002 | 1 | 65 | 35 | 21 |
| cyclo-YW$_D$KTF.(N—CH$_3$)Hcy(CH$_2$CO.TGGC.amide) | 3.81 | 4.7 | 0.04 | 30 | 26 | 95 | 30 |
| cyclo-(N—CH$_3$)-FW$_D$KTF(N—CH$_3$)Hcy(CH$_2$CO.β-Dap.KCT(ol)) | 3.58 | 43.4 | 0.04 | 5 | 51 | 33 | 90 |
| cyclo-YW$_D$KTF.(N—CH$_3$)Hcy(CH$_2$CO.δ-Orn.GC.amide)] | 1.8 | 1.5 | 0.023 | 47 | 15 | 95 | 29 |
| cyclo-YW$_D$KTF.(N—CH$_3$)Hcy(CH$_2$CO.GGCH.amide) | 0.8 | 3 | 0.009 | 42 14 | 32 | 8.7 | |
| cyclo-YW$_D$KTF.(N—CH$_3$)Hcy(CH$_2$CO.GGC.F(4-NH$_2$).amide) | 0.7 | 1.9 | 0.07 | 33 | 7 | 9 | 2.8 |

It should be understood that the foregoing disclosure emphasizes certain specific embodiments of the invention and that all modifications or equivalents thereto are within the spirit and scope of the invention as set forth in the appended claims.

What is claimed is:

1. A compound comprising a somatostatin receptor-binding peptide having a formula cyclo-B$^1$-B$^2$-B$^3$-B$^4$-C-A wherein B$^1$ is Phe, Tyr, Nal, Ain, or a substituted derivative thereof;

B$^2$ is Trp or a substituted derivative thereof;

B$^3$ is Lys, Hly, Achxa, Amf, Aec, Apc, Aes, Aps or a substituted derivative thereof;

B$^4$ is Thr, Ser, Val, Phe, Ile, Abu, Nle, Leu, Nva, or Aib;

C is an L-α-amino acid;

A is an N-alkyl-α-amino acid or an N-substituted alkyl-β-amino acid, wherein A comprises a sidechain containing a sulfur atom;

wherein A and B$^1$ are covalently linked though an amino terminus of B$^1$ and a carboxyl terminus of A to form a cyclic peptide.

2. The compound of claim 1, wherein A is an N-methyl-α-amino acid.

3. The compound of claim 2, wherein A is selected from the group consisting of (N—CH$_3$)Cys, (N—CH$_3$)Hcy, (N—CH$_3$)Tyr, (N—CH$_3$)Tyr, and (N—CH$_3$)Tyr (CH$_2$CH$_2$SH).

4. The compound of claim 3, wherein A is selected from the group consisting of (N—CH$_3$)Cys, (N—CH$_3$)Hcy, and (N—CH$_3$)Tyr, and C is selected from the group consisting of L-methionine, L-phenylalanine, and a substituted derivative of L-phenylalanine.

5. The compound of claim 4, wherein A is selected from the group consisting of (N—CH$_3$)Cys and (N—CH$_3$)Hcy, and C is selected from the group consisting of L-methionine, L-phenylalanine, and a substituted derivative of L-phenylalanine.

6. The compound of claim 5, wherein A is (N—CH$_3$)Hcy and C is L-phenylalanine.

7. The compound of claim 1, having the formula:

cyclo-Tyr-D-Trp-Lys-Thr-Phe-(N—CH$_3$)Hcy.

8. The compound of claim 1, wherein a chelator or radiometal ligand is covalently linked to a sidechain of A.

9. The compound of claim 8, wherein the chelator has a formula:

β-Dap.Xaa.Cys.Zaa wherein

Xaa is an L-αamino acid, and

Zaa is an α-amino acid, an α-amino acid amide, an aminoethylether, a β-aminol, or a peptide containing from two to ten α-amino acids, said peptide having a carboxyl terminal α-amino acid, α-amino acid amide, aminoethylether, or β-aminol.

10. The compound of claim 8, wherein the chelator is selected from the group consisting of 1,4,7,10- tetraazacyclododecane-1,4,7-triacetic acid, 1,4,7,10-tetraazacyclododecane-1,4,7,10-tetraacetic acid, a substituted derivative of 1,4,7,10-tetraazacyclododecane-1,4,7-triacetic acid, and a substituted derivative of 1,4,7,10-tetraazacyclododecane-1,4,7,10-tetraacetic acid.

11. The compound of claim 8, wherein the ligand is a hydrazino nicotinamide moiety.

12. A compound having a formula cyclo-$B^1$-$B^2$-$B^3$-$B^4$-C-(N—$CH_3$)Hcy-X wherein $B^1$ is Phe, Tyr, Nal, Ain, or a substituted derivative thereof;

$B^2$ is Trp or a substituted derivative thereof;

$B^3$ is Lys, Hly, Achxa, Amf, Aec, Apc, Aes, Aps or a substituted derivative thereof;

$B^4$ is Thr, Ser, Val, Phe, Ile, Abu, Nle, Leu, Nva, or Aib;

C is L-methionine, L-phenylalanine, or a substituted derivative of L-phenylalanine;

X is a H, a chelator, or a radiometal ligand;

wherein $B^1$ and (N—$CH_3$)Hcy are covalently linked through an amino terminus of $B^1$ and a carboxyl terminus of (N—$CH_3$)Hcy to form a cyclic peptide and X is linked to the (N—$CH_3$)Hcy residue through a sidechain sulfur atom.

13. The compound of claim 12, wherein X is a chelator having a formula:

β-Dap.Xaa.Cys.Zaa wherein

Xaa is an L-α-amino acid, and

Zaa is an amino acid, an amino acid amide, an aminoethylether, a β-aminol, or a peptide containing from two to ten amino acids, said peptide having a carboxyl terminal amino acid, amino acid amide, aminoethylether, or β-aminol.

14. The compound of claim 13, wherein Xaa is selected from the group consisting of serine, diaminobutyric acid, histidine, arginine, tyrosine, iodotyrosine, bromotyrosine, chlorotyrosine, O-alkyl-tyrosine where alkyl represents $C_1$ to $C_4$ alkyl, hydroxyltyrosine, aminotyrosine, phenylalanine, 4-fluorophenylalanine, 4-chlorophenylalanine, 4-bromophenylalanine, 4-iodophenylalanine, 4-nitrophenylalanine, 4-aminophenylalanine, $N^4$—R-4-aminophenylalanine, $N^4$—R, $N^4$—R'-4-aminophenylalanine, or 3-R'-4-aminophenylalanine where R is $C_1$ to $C_4$ alkyl and R' is selected from the group consisting of H, $C_1$ to $C_4$ alkyl, amino, hydroxyl, NH-alkyl wherein alkyl represents $C_1$ to $C_4$ alkyl, NH-acyl, O-alkyl wherein alkyl represents $C_1$ to $C_4$ alkyl, O-acyl, S-alkyl wherein alkyl represents $C_1$ to $C_4$ alkyl, SO-alkyl and $SO_2$-alkyl wherein alkyl represents $C_1$ to $C_4$ alkyl, $SO_3H$, $CO_2H$, $CO_2$-alkyl wherein alkyl represents $C_1$ to $C_4$ alkyl, and CONH-alkyl wherein alkyl represents $C_1$ to $C_4$ alkyl.

15. The compound of claim 12, wherein X is a hydrazino nicotinamide moiety.

16. The compound of claim 12, wherein X is a chelator selected from the group consisting of 1,4,7,10-tetraazacyclododecane-1,4,7-triacetic acid, 1,4,7,10-tetraazacyclododecane-1,4,7,10-tetraacetic acid, a substituted derivative of 1,4,7,10-tetraazacyclododecane-1,4,7-triacetic acid, or a substituted derivative of 1,4,7,10-tetraazacyclododecane-1,4,7,10-tetraacetic acid.

17. A radiopharmaceutical comprising the compound of any of claims 1 through 16 and a radioisotope selected from the group consisting of an α-emitting radionuclide, a β-emitting radionuclide, a β-/γ-emitting radionuclide, a positron emitting radionuclide, and a γ-emitting radionuclide.

18. The radiopharmaceutical of claim 17, wherein the radioisotope is selected from the group consisting of $^{68}$Ga, $^{67}$Ga, $^{67}$Cu, $^{47}$Sc, $^{111}$In, $^{99m}$Tc, $^{186}$Re, $^{188}$Re, $^{212}$Bi, $^{213}$Bi, $^{90}$Y, $^{64}$Cu, $^{153}$Sm, $^{94m}$Tc, $^{166}$Ho, $^{223}$Ra, $^{225}$Ac.

19. The radiopharmaceutical of claim 17, wherein the radioisotope is selected from the group consisting of $^{18}$F, $^{125}$I, $^{131}$I, $^{123}$I, and $^{211}$At.

20. A compound having a formula selected from the group consisting of:

cyclo-Tyr-D-Trp-Lys-Thr-Phe-(N—$CH_3$)Hcy($CH_2$CO-β-Dap-Tyr-Cys-Thr(ol));

cyclo-Tyr-D-Trp-Lys-Thr-Phe-(N—$CH_3$)Hcy($CH_2$CO-β-Dap-Phe$(_4$-F)-Cys-Thr(ol));

cyclo-Tyr-D-Trp-Lys-Thr-Phe-(N—$CH_3$)Hcy($CH_2$CO-β-Dap-Phe$(_4NH_2)$-Cys-Thr-Ser);

cyclo-Tyr-D-Trp-Lys-Thr-Phe-(N—$CH_3$)Hcy($CH_2$CO-β-Dap-Dab-Cys-Thr);

cyclo-Tyr-D-Trp-Lys-Thr-Phe-(N—$CH_3$)Hcy($CH_2$CO-β-Dap-Phe$(_4$-$NH_2)$-Cys-Thr);

cyclo-Tyr-D-Trp-Lys-Thr-Phe-(N—$CH_3$)Hcy($CH_2$CO-β-Dap-Phe$(_4$-$NH_2)$-Cys-Thr(ol));

cyclo-Tyr-D-Trp-Lys-Thr-Phe-(N—$CH_3$)Hcy($CH_2$CO-Gly-Gly-Cys-Lys-Thr(ol));

cyclo-Tyr-D-Trp-Lys-Thr-Phe-(N—$CH_3$)Hcy($CH_2$CO-β-Dap-His-Cys-Thr(ol));

cyclo-Tyr-D-Trp-Lys-Thr-Phe-(N—$CH_3$)Hcy($CH_2$CO-β-Dap-Arg-Cys-Thr(ol));

cyclo-Tyr-D-Trp-Lys-Thr-Phe-(N—$CH_3$)Hcy($CH_2$CO-β-Dap-Gly-Cys-Lys-$NH_2$);

cyclo-Tyr-D-Trp-Lys-Thr-Phe-(N—$CH_3$)Hcy($CH_2$CO-β-Dap-Ser-Cys-Thr(ol));

cyclo-Tyr-D-Trp-Lys-Thr-Phe-(N—$CH_3$)Hcy($CH_2$CO-β-Dap-Dab-Cys-Thr(ol));

cyclo-Tyr-D-Trp-Lys-Thr-Phe-(N—$CH_3$)Hcy($CH_2$CO-β-Dap-Gly-Cys-Thr(ol));

cyclo-Tyr-D-Trp-Lys-Thr-Phe-(N—$CH_3$)Hcy($CH_2$CO-β-Dap-Dab-Cys-Ser(ol));

cyclo-Tyr-D-Trp-Lys-Thr-Phe-(N—$CH_3$)Hcy($CH_2$CO-Gly-Gly-Cys-Lys-$NH_2$);

cyclo-Tyr-D-Trp-Lys-Thr-Phe-(N—$CH_3$)Hcy($CH_2$CO-Gly-Gly-Cys-Arg-$NH_2$);

cyclo-Tyr-D-Trp-Lys-Thr-Phe-(N—$CH_3$)Hcy($CH_2$CO-Ser-Ser-Cys-Lys-$NH_2$);

cyclo-Tyr-D-Trp-Lys-Thr-Phe-(N—$CH_3$)Hcy($CH_2$CO-Ser-Ser-Cys-Arg-$NH_2$);

cyclo-Tyr-D-Trp-Lys-Thr-Phe-(N—$CH_3$)Hcy($CH_2$CO-Ser-Ser-Cys-Lys-Thr-(ol));

cyclo-Tyr-D-Trp-Lys-Thr-Phe-(N—$CH_3$)Hcy($CH_2$CO-Ser-Ser-Cys-Dap-$NH_2$);

cyclo-

Tyr-D-Trp-Lys-Thr-Phe-(N—CH$_3$)Hcy(CH$_2$CO-Ser-Ser-Cys-NH(CH$_2$ $_{CH2\ O}$)$_2$ $_{CH2\ CH2\ NH2}$);

cyclo-Tyr-D-Trp-Lys-Thr-Phe-(N—CH$_3$)Hcy(CH$_2$CO-β-Dap-Ser-Cys-Thr-NH(CH$_2$ $_O$)$_2$ $_{CH2\ CH2\ NH2}$);

cyclo-Tyr-D-Trp-Lys-Thr-Phe-(N—CH$_3$)Hcy(CH$_2$CO-Gly-Lys-Cys-NH$_2$);

cyclo-Tyr-D-Trp-Lys-Thr-Phe-(N—CH$_3$)Hcy(CH$_2$CO-Ser-Lys-Cys-NH$_2$);

cyclo-Tyr-D-Trp-Lys-Thr-Phe-(N—CH$_3$)Hcy(CH$_2$CO-Lys-Gly-Cys-NH$_2$);

cyclo-Tyr-D-Trp-Lys-Thr-Phe-(N—CH$_3$)Hcy(CH$_2$CO-Ser-Dab-Cys-Ser-(ol));

cyclo-Tyr-D-Trp-Lys-Thr-Phe-(N—CH$_3$)Hcy(CH$_2$CO-Ser-Dab-Cys-NH$_2$);

cyclo-Tyr-D-Trp-Lys-Thr-Phe-(N—CH$_3$)Hcy(CH$_2$CO-Gly-Gly-Cys-His-NH$_2$);

cyclo-Tyr-D-Trp-Lys-Thr-Phe-(N—CH$_3$)Hcy(CH$_2$CO-Gly-Gly-Cys-Phe-(4-NH$_2$)—NH$_2$);

cyclo-Tyr-D-Trp-Lys-Thr-Phe-(N—CH$_3$)Hcy(CH$_2$CO-β-Dap-Orn-Cys-Thr(ol));

cyclo-Tyr-D-Trp-Lys-Thr-Phe-(N—CH$_3$)Hcy(CH$_2$CO-β-Dap-Dap-Cys-Thr(ol));

cyclo-Tyr-D-Trp-Lys-Thr-Phe-(N—CH$_3$)Hcy(CH$_2$CO-β-Dap-Lys-Cys-Thr(ol));

cyclo-Tyr-D-Trp-Lys-Thr-Phe-(N—CH$_3$)Hcy(CH$_2$CO-Ser-Ser-Cys-NHCH$_2$ $_{CH2\ OCH2\ CH2\ NH2}$);

cyclo-Tyr-D-Trp-Lys-Thr-Phe-(N—CH$_3$)Hcy(CH$_2$CO-β-Dap-Lys-Cys-NH$_2$);

cyclo-Tyr-D-Trp-Lys-Thr-Phe-(N—CH$_3$)Hcy(CH$_2$CO-δ-Orn-Gly-Cys-NH$_2$); and cyclo-Tyr-D-Trp-Lys-Thr-Phe-(N—CH$_3$)Hcy(CH$_2$CO-Thr-Gly-Gly-Cys-NH$_2$).

21. A radiopharmaceutical comprising the compound of claim 20 and a radioisotope selected from the group consisting of $^{99m}$Tc, $^{186}$Re, $^{188}$Re, $^{212}$Bi, and $^{213}$Bi.

22. A compound having a formula:

cyclo-Tyr-D-Trp-Lys-Thr-Phe-(N—CH$_3$)Hcy(Ch$_2$CO-β-Dap-Phe(4-NH$_2$)-Cys-Thr-Ser).

23. A radiopharmaceutical comprising the compound of claim 22 and $^{99m}$Tc.

24. A radiopharmaceutical comprising the compound of claim 22 and $^{188}$Re.

25. A complex of $^{99m}$Tc and a compound having a formula:

cyclo-Tyr-D-Trp-Lys-Thr-Phe-(N—CH$_3$)Hcy(CH$_2$CO-β-Dap-Phe-(4-NH$_2$)-Cys-Thr-Ser).

26. A complex of $^{186}$Re or $^{188}$Re and a compound having a formula:

cyclo-Tyr-D-Trp-Lys-Thr-Phe-(N—CH$_3$)Hcy(CH$_2$CO-β-Dap-Phe(4-NH$_2$)-Cys-Thr-Ser).

27. A kit for preparing a radiopharmaceutical preparation, said kit comprising a sealed vial containing a predetermined quantity of the compound of any of claims 1 through 16 and an effective amount of a reducing agent to label the compound with $^{99m}$Tc, $^{186}$Re or $^{188}$Re.

28. A kit for preparing a radiopharmaceutical preparation, said kit comprising a sealed vial containing a predetermined quantity of the compound of claim 20 and an effective amount of a reducing agent to label the compound with $^{99m}$Tc, $^{186}$Re or $^{188}$Re.

29. A kit for preparing a radiopharmaceutical preparation, said kit comprising a sealed vial containing a predetermined quantity of the compound of claim 22 and an effective amount of a reducing agent to label the compound with $^{99m}$Tc, $^{186}$Re or $^{188}$Re.

30. A kit comprising a sealed vial containing a predetermined quantity of the compound of any of claims 1 through 16.

31. A kit comprising a sealed vial containing a predetermined quantity of the compound of claim 20.

32. A kit comprising a sealed vial containing a predetermined quantity of the compound of claim 22.

33. A method of imaging a site within a mammalian body comprising the steps of:
  a) radiolabeling the compound of any of claims 1 through 16 with $^{99m}$Tc;
  b) administering an effective diagnostic amount of the radiolabeled compound to the body; and
  c) detecting $^{99m}$Tc accumulated at the site.

34. A method of imaging a site within a mammalian body comprising the steps of:
  a) radiolabeling the compound of claim 20 with $^{99m}$Tc;
  b) administering an effective diagnostic amount of the radiolabeled compound to the body; and
  c) detecting $^{99m}$Tc accumulated at the site.

35. A method of imaging a site within a mammalian body comprising the steps of:
  a) administering an effective diagnostic amount of the radiopharmaceutical of claim 23 to the body; and
  c) detecting $^{99m}$Tc accumulated at the site.

36. A method of treating an animal suffering a somatostatin-responsive disease, comprising the steps of:
  a) radiolabeling the compound of any of claims 1 through 16 with $^{186}$Re, $^{188}$Re, $^{212}$Bi, $^{213}$Bi, $^{90}$Y, $^{153}$Sm, $^{47}$Sc, $^{68}$Ga, $^{94m}$Tc, $^{67}$Cu, 166Ho, $^{223}$Ra, $^{225}$Ac, $^{18}$F, $^{125}$I, $^{131}$I, $^{123}$I, or $^{211}$At; and
  b) administering a therapeutically effective amount of the radiolabeled compound to the animal.

37. A method of treating an animal suffering a somatostatin-responsive disease, comprising the steps of:
  a) radiolabeling the compound of claim 20 with $^{186}$Re, $^{188}$Re, $^{212}$Bi, or $^{213}$Bi; and
  b) administering a therapeutically effective amount of the radiolabeled compound to the animal.

38. A method of treating an animal suffering a disease wherein somatostatin receptors are up-regulated, comprising the steps of:
  a) radiolabeling the compound of claim 20 with $^{186}$Re, $^{188}$Re, $^{212}$Bi, or $^{213}$Bi; and b) administering an effective therapeutic amount of the radiolabeled compound to the animal.

39. A method of treating an animal suffering a somatostatin-responsive disease, comprising the step of:
administering a therapeutically effective amount of the radiopharmaceutical of claim 24 to the animal.

40. A method of treating an animal suffering a somatostatin-responsive disease, comprising the step of administering a therapeutically effective amount of the compound of any of claims 1 through 16 to the animal.

41. A method of treating an animal suffering a somatostatin-responsive disease, comprising the step of administering an effective therapeutic amount of the compound of claim 20 to the animal.

42. A method of treating an animal suffering a somatostatin-responsive disease, comprising the step of administering an effective therapeutic amount of the compound of claim 22 to the animal.

43. A method of treating a tumor in a mammal comprising the steps of:
a) combining a first aliquot of the compound of any of claims 1 through 16 with $^{99m}$Tc to form a diagnostic agent;
b) administering an effective diagnostic amount of the diagnostic agent to the mammal;
c) detecting $^{99m}$Tc accumulated in the mammal, thereby determining the presence of a SSTR-expressing tumor;
d) combining a second aliquot of said compound with a cytotoxic radioisotope to form a radiotherapeutic agent; and
e) administering a therapeutically effective amount of the radiotherapeutic agent to the mammal.

44. A method of treating a tumor in a mammal comprising the steps of:
a) combining a first aliquot of the compound of claim 20 with $^{99m}$Tc to form a diagnostic agent;
b) administering an effective diagnostic amount of the diagnostic agent to the mammal;
c) detecting $^{99m}$Tc accumulated in the mammal, thereby determining the presence of a SSTR-expressing tumor;
d) combining a second aliquot of said compound with a cytotoxic radioisotope to form a radiotherapeutic agent; and
e) administering a therapeutically effective amount of the radiotherapeutic agent to the mammal.

45. A method of treating a tumor in a mammal comprising the steps of:
a) combining a first aliquot of a compound having a formula:

cyclo-Tyr-D-Trp-Lys-Thr-Phe-(N—CH$_3$)Hcy(CH$_2$CO-β-Dap-Phe (4-NH$_2$)-Cys-Thr-Ser)

with $^{99m}$Tc to form a diagnostic agent;
b) administering an effective diagnostic amount of the diagnostic agent to the mammal;
c) detecting $^{99m}$Tc accumulated in the mammal, thereby determining the presence of a SSTR-expressing tumor;
d) combining a second aliquot of said compound with a cytotoxic radioisotope to form a radiotherapeutic agent; and
e) administering a therapeutically effective amount of the radiotherapeutic agent to the mammal.

* * * * *